US011639494B2

(12) United States Patent
Truong et al.

(10) Patent No.: US 11,639,494 B2
(45) Date of Patent: May 2, 2023

(54) CULTURE MEDIUM

(71) Applicant: Vitrolife Sweden AB, Gothenburg (SE)

(72) Inventors: Thi Truong, West Brunswick (AU); David Gardner, West Brunswick (AU)

(73) Assignee: Vitrolife Sweden AB, Gothenburg (SE)

(*) Notice: Subject to any disclaimer, the term of this patent is extended or adjusted under 35 U.S.C. 154(b) by 423 days.

(21) Appl. No.: 15/754,679

(22) PCT Filed: Aug. 24, 2016

(86) PCT No.: PCT/EP2016/070005
§ 371 (c)(1),
(2) Date: Feb. 23, 2018

(87) PCT Pub. No.: WO2017/032811
PCT Pub. Date: Mar. 2, 2017

(65) Prior Publication Data
US 2019/0136182 A1    May 9, 2019

(30) Foreign Application Priority Data

Aug. 24, 2015 (GB) .................................. 1515015
Feb. 26, 2016 (GB) .................................. 1603407
Apr. 28, 2016 (GB) .................................. 1607414

(51) Int. Cl.
C12N 5/073       (2010.01)
C12N 5/076       (2010.01)
C12N 5/071       (2010.01)

(52) U.S. Cl.
CPC .......... *C12N 5/0604* (2013.01); *C12N 5/061* (2013.01); *C12N 5/0608* (2013.01); *C12N 2500/02* (2013.01); *C12N 2500/30* (2013.01); *C12N 2500/32* (2013.01); *C12N 2517/10* (2013.01)

(58) Field of Classification Search
None
See application file for complete search history.

(56) References Cited

U.S. PATENT DOCUMENTS

| 6,048,728 | A  | * | 4/2000  | Inlow ................... C12N 5/0037 435/325 |
| 6,130,086 | A  |   | 10/2000 | Nakazawa et al. |
| 2005/0260752 | A1 |   | 11/2005 | Wilding et al. |
| 2006/0188866 | A1 | * | 8/2006  | Atamna ................... A61K 8/49 435/2 |
| 2010/0137676 | A1 |   | 6/2010  | Goldstein |
| 2013/0344595 | A1 |   | 12/2013 | Gardner et al. |
| 2014/0134732 | A1 | * | 5/2014  | Ashton ................ C12N 5/0619 435/377 |
| 2018/0355312 | A1 | * | 12/2018 | Lane ........................ A61P 15/08 |

FOREIGN PATENT DOCUMENTS

| GB | 1486468 A       | 9/1977  |           |
|----|------------------|---------|-----------|
| GB | 2517194 A       | 2/2015  |           |
| KR | 20090002880 A   | 1/2009  |           |
| WO | WO-00/11968 A1  | 3/2000  |           |
| WO | WO-2005/085422 A1 | 9/2005 |           |
| WO | WO-2006/089301 A2 | 8/2006 |           |
| WO | WO-2006089301 A2 * | 8/2006 | ............. A61K 45/06 |
| WO | WO-2006/116034 A1 | 11/2006 |          |
| WO | WO-2007/037682 A1 | 4/2007  |          |
| WO | WO-2007/147590 A2 | 12/2007 |          |
| WO | WO-2008/134220 A1 | 11/2008 |          |
| WO | WO-2013/113658 A1 | 8/2013  |          |

OTHER PUBLICATIONS

Ali et al. "Antioxidant requirements for bovine oocytes varies during in vitro maturation, fertilization and development." Theriogenology 59.3-4 (2003): 939-949. (Year: 2003).*
Gstraunthaler "Alternatives to the use of fetal bovine serum: serum-free cell culture." ALTEX-Alternatives to Animal Experimentation 20.4 (2003): 275-281. (Year: 2003).*
Xiong et al. "In vitro N-acetyl-L-cysteine promotes proliferation and suppresses interleukin-8 expression in adipose-derived stem cells." Aesthetic Plastic Surgery 36.5 (2012): 1260-1265. (Year: 2012).*
Christianson et al., Embryo catheter loading and embryo culture techniques: results of a worldwide Web-based survey, J. Assist. Reprod. Genet., 31(8):1029-36 (2014).
Desai et al., Use of Synthetic Serum Substitute and alpha-minimum essential medium for the extended culture of human embryos to the blastocyst stage, Hum. Reprodc., 12(2):328-35 (1997).
Gardner et al., Analysis of metabolism to select viable human embryos for transfer, Fertil. Steril., 99(4):1062-72 (2013).
Gardner et al., "In vitro culture of human blastocytes", pp. 378-388 IN: Jansen et al. (eds.), Towards Reproductive Certainty: Fertility & Genetics Beyond 1999, New York: The Parthenon Publishing Group (1999).
Gott et al., Non-invasive measurement of pyruvate and glucose uptake and lactate production by single human preimplantation embryos, Hum. Reprod., 5(1):104-8 (1990).
International Application No. PCT/EP2016/070005, International Preliminary Report on Patentability, dated Feb. 27, 2018.
International Application No. PCT/EP2016/070005, International Search Report and Written Opinion, dated Nov. 18, 2016.
Leese et al., Pyruvate and glucose uptake by mouse ova and preimplantation embryos, J. Reprod. Fertil., 72(1):9-13 (1984).
Legge et al., Free radical scavengers ameliorate the 2-cell block in mouse embryo culture, Hum. Reprod., 6(6):867-71 (1991).
Nasr-Esfahani et al., Quantitative analysis of cellular glutathione in early preimplantation mouse embryos developing in vivo and in vitro, Hum. Reprod., 7(9):1281-90 (1992).

(Continued)

Primary Examiner — Emily A Cordas
(74) Attorney, Agent, or Firm — Marshall, Gerstein & Borun LLP

(57) ABSTRACT

An embryo, gamete or stem cell culture medium comprising: a) acetyl-carnitine at a concentration of about 5 to about 50 μM; and b) lipoic acid or a derivative thereof at a concentration of about 2.5 to about 40 μM. The culture medium may optionally further comprises acetyl-cysteine at a concentration of about 5 to about 50 μM.

12 Claims, 8 Drawing Sheets

(56) References Cited

OTHER PUBLICATIONS

Noda et al., Involvement of superoxide radicals in the mouse two-cell block, Mol. Reprod. Dev., 28(4):356-60 (1991).

Payne et al., Addition of superoxide dismutase and catalase does not necessarily overcome developmental retardation of one-cell mouse embryos during in-vitro culture, Reprod. Fertil. Dev., 4(2):167-74 (1992).

Pribenszky et al., Prediction of in-vitro developmental competence of early cleavage-stage mouse embryos with compact time-lapse equipment, Reprod. Biomed. Online, 20(3):371-9 (2010).

Silva et al., Antioxidant supplementation during in vitro culture improves mitochondrial function and development of embryos from aged female mice, Reprod. Fertil. Dev., 27(6):975-83 (2015).

Wahlsten et al., Application of a morphological time scale to hereditary differences in prenatal mouse development, 42:79-92 (1977).

Yamada et al., Beneficial effects of acetyl-L-carnitine treatment during IVM on post-fertilization development of bovine oocytes in vitro, Reprod. Fertility Dev., 18(2):280-1 (2005).

Zhang et al., Synthesis and anticancer evaluation of alpha-lipoic acid derivatives, Bioorg. Med. Chem. Lett., 20(10):3078-83 (2010).

McKiernan et al., Culture of one-cell hamster embryos with water soluble vitamins: pantothenate stimulates blastocyst production, Hum. Reprod., 15(1):157-64 (2000).

Truong et al., Antioxidants improve mouse preimplantation embryo development and viability, Hum. Reprod., 31 (7):1445-54 (2016).

Shen We et al., R-alpha-lipoic acid and acetyl-L-carnitine complementarily promote mitochondrial biogenesis in murine 3T3-L1 adipocyte, Diabetologia, 2008, vol. 51, pp. 165-174.

Martins W P et al., Blastocyst vs. Cleavage-Stage Embryo Transfer: Systematic Review and Meta-Analysis of Reproductive Outcomes, Ultrasound Obstet Gynecol, 2017, vol. 49, pp. 583-591.

Ailamazyan et al. "Co-cultivation of the human embryo with the endometrium: optimization of in vitro fertilization", Journal of Obstetrics and Women's Diseases, LXI(4):16-22 (2012).

\* cited by examiner

CULTURE MEDIUM

CROSS-REFERENCE TO RELATED APPLICATION

This application is a National Stage application of International Patent Application No. PCT/EP2016/070005, filed Aug. 24, 2016, which claims the priority to United Kingdom Application No. 1515015.4, filed Aug. 24, 2015, United Kingdom Application No. 1603407.6, filed Feb. 26, 2016 and United Kingdom Application No. 1607414.8, filed Apr. 28, 2016. The entire contents of these applications are incorporated herein by reference in their entirety.

TECHNICAL FIELD

The present invention relates to a culture medium for an embryo, a gamete or a stem cell.

BACKGROUND

Infertility affects more than 80 million people worldwide. It is estimated that 10% of all couples experience primary or secondary infertility. Assisted Reproduction Treatment (ART) is an elective medical treatment that may provide a couple who has been otherwise unable to conceive a chance to establish a pregnancy. It is a process in which eggs (oocytes) are taken from a woman's ovaries and then fertilized with sperm in the laboratory. The embryos created in this process are then placed into the uterus for potential implantation.

Despite advances in ARTs, the success rates remain low with live births per implantation at ~30%. Many factors impact successful ART outcome particularly since the in vitro culture of embryos cannot simulate the physiological conditions in vivo exactly. For instance reactive oxygen species (ROS) produced through the handling, manipulation and culture of gametes in an in vitro environment can lead to the development of oxidative stress which can adversely affect embryo quality and loss of viability. A key contributor of ROS in vitro is the oxygen concentration that embryos are cultured under. Embryo collection and culture at atmospheric oxygen (~20%) creates a hyperoxic environment condition that has been implicated in the increase production of exogenous ROS which subsequently leads to oxidative stress. The effects of oxidative stress on embryos collected and cultured at 20% oxygen has been shown to negatively affect their gene expression, alter the resultant proteome, and perturb metabolism. Even a brief exposure to atmospheric oxygen can adversely impact embryo development resulting in delayed cleavage divisions. However, despite growing evidence that high oxygen concentration is detrimental to embryo development and viability, a considerable number of IVF cycles worldwide are still performed at atmospheric oxygen.

Although embryo culture performed at 5% oxygen may alleviate some of damaging effects of oxidative stress, 5% oxygen concentration still leads to oxidative stress. Furthermore, all gametes are exposed to atmospheric oxygen during their collection and processing. Despite evidence that high oxygen concentration is detrimental to human embryo development and viability, it has been reported that only 25% of IVF cycles worldwide are performed exclusively in 5% oxygen, with 34% of clinics reporting the use of 5% oxygen for specific stages of embryo culture, and the remainder of clinics employing 20% oxygen exclusively (Christianson, et al., 2014 J. Assist Reprod. Genet. 31: 1029-1036).

Moreover the effects of oxidative stress on embryos caused by high levels of exogenous ROS may be compounded due to in vitro cultures crucially lacking the physiological mechanisms necessary for maintaining tight regulation over ROS levels. Certainly endogenous ROS is produced in vivo by the gametes and embryos and low levels are necessary for the proper regulation of gamete function and development. However unlike in in vitro conditions, excess ROS in vivo is quenched by an elegant antioxidant defence system that provides repair and protection against oxidative damage. Thus under physiological conditions a fine equilibrium/homeostasis is maintained between systemic ROS and antioxidant capacity. This balance is disrupted in vitro, and as in the case of culturing embryos at 20% oxygen, the build-up of exogenous ROS and the lack of protective mechanisms inevitably lead to oxidative stress. ROS in vivo is neutralised by the innate antioxidant system comprising of enzymes and non-enzymes. Enzymatic antioxidants, including catalase, glutathione peroxidase/reductase and superoxide dismutase (SOD) are found in cellular cytoplasm, endometrial glandular cells and mitochondria and confer protection by scavenging ROS. Non-enzymatic antioxidants such as vitamins (A, B, C and E), pyruvate, glutathione (GSH) and hypotaurine have been found in the ovary, seminal plasma, endometrial epithelium and follicular and tubal fluid, and prevent ROS formation by terminating oxidative chain reactions. As in vitro culture lack these innate antioxidants, supplementation of various antioxidants to the culture media have been used as a treatment to keep ROS levels in check and prevent oxidative damage to gametes and embryos. Oxidative stress in stem cell culture is also a documented problem.

Although the effects of individual antioxidants on embryo development have been reported, there has been relatively limited research on the effects of antioxidants present as a group in the medium on embryo development. There are conflicting reports on the beneficial effects of antioxidants in the culture media (Legge and Sellens, *Hum Reprod* 1991; 6: 867-871; Nasr-Esfahani and Johnson, *Hum Reprod* 1992; 7: 1281-1290; Noda, et al., *Mol Reprod Dev* 1991; 28: 356-360; Payne, et al., *Reprod Fertil Develop* 1992; 4: 167-174).

Finding culture media that enhance development of embryos, and proliferation and differentiation of stem cells or for maintaining or enhancing viability of gametes has been a challenge.

SUMMARY OF THE INVENTION

According to a first aspect the present invention provides an embryo, a gamete or stem cell culture medium comprising:
  a) acetyl-carnitine at a concentration of about 5 to about 50 μM; and
  b) lipoic acid or a derivative thereof at a concentration of about 2.5 to about 40 μM.

In another aspect the present invention provides an embryo, a gamete or stem cell culture medium comprising:
  a) acetyl-carnitine at a concentration of about 5 to about 50 μM;
  b) lipoic acid or a derivative thereof at a concentration of about 2.5 to about 40 μM; and
  c) acetyl-cysteine at a concentration of about 5 to about 50 μM.

In a further aspect the present invention provides a method for handling and/or manipulating and/or culturing an embryo and/or a gamete, or a stem cell, the method comprising handling and/or manipulating and/or culturing the embryo and/orgamete or stem cell in a culture medium according to the present invention.

The present invention provides in another aspect a method of reducing or preventing oxidative stress and/or reducing or preventing free radical formation (e.g. reactive oxygen species (ROS) formation) and/or increasing levels of antioxidant capacity in an embryo and/or gamete or stem cell cultured in vitro and/or to improve development of an embryo cultured in vitro or to improve the proliferation and differentiation of a stem cell cultured in vitro or to improve gamete health and/or viability, the method comprising handling and/or manipulating and/or culturing the embryo and/or gamete, or stem cell in a medium according to the present invention.

In another aspect the present invention provides a method of in vitro fertilisation comprising culturing gametes, fertilizing oocytes with sperm, and/or culturing an embryo in a medium according to present invention. In one embodiment preferably said method of in vitro fertilisation does not encompass implantation of the embryo in a human or animal body.

The present invention yet further provides use of the combination of acetyl-carnitine and lipoic acid or a derivative thereof in an embryo culture medium and/or a gamete culture medium, or stem cell culture medium.

In another aspect the present invention provides the use of the combination of acetyl-carnitine, lipoic acid or a derivative thereof and acetyl-cysteine in an embryo culture medium and/or a gamete culture medium or stem cell culture medium.

The present invention also provides use of an embryo culture medium and/or a gamete culture medium, or stem cell culture medium, according to the present invention to reduce or prevent oxidative stress and/or free radical formation and/or increase levels of antioxidant capacity in an embryo or stem cell cultured in vitro and/or to improve the development of an embryo cultured in vitro or the proliferation and differentiation of a stem cell cultured in vitro or to improve gamete health and/or viability.

In a yet further aspect of the present invention there is provided use of an embryo culture medium and/or a gamete culture medium according to the present invention to improve the success rate of in vitro fertilisation. In one embodiment, the use of the embryo culture medium and/or gamete culture medium according to the present invention to improve the success rate of in vitro fertilisation does not encompass implantation of the embryo in a human or animal body.

In a further aspect the present invention provides a culture medium according to the present invention for use in culturing an embryo, a gamete or a stem cell.

BRIEF DESCRIPTION OF THE DRAWINGS

Embodiments of the invention will now be described, by way of example only, with reference to accompanying drawings, in which.

DETAILED DESCRIPTION

Figure 1A:
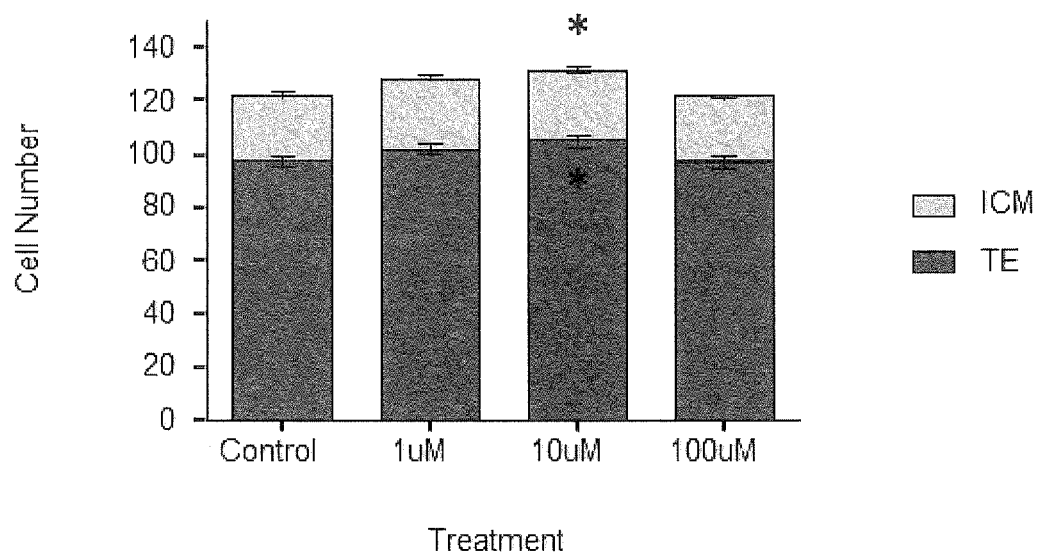
FIG. 1a shows group embryo development in 20% oxygen with acetyl carnitine at different dosages.

The present invention is predicated upon the surprising finding that specific combinations of acetyl-carnitine at a concentration of about 5 to about 50 µM and lipoic acid or a derivative thereof at a concentration of about 2.5 to about 40 µM, and particularly when combined with acetyl-cysteine at a concentration of about 5 to about 50 µM, significantly improved the development of an embryo cultured in vitro or the proliferation and differentiation of a stem cell cultured in vitro or the health and viability of gametes and/or the fertilization of an oocyte by a sperm.

The present invention relates to a gamete culture media, an embryo culture medium or stem cell culture medium comprising:
 a) acetyl-carnitine at a concentration of about 5 to about 50 µM; and
 b) lipoic acid or a derivative thereof at a concentration of about 2.5 to about 40 µM.

In one embodiment the gamete culture medium, embryo culture medium or stem cell culture medium according to the present invention further comprises acetyl-cysteine at a concentration of about 5 to about 50 µM.

In one embodiment acetyl-carnitine is present in the culture medium of the present invention at a concentration of about 5 µM to about 20 µM.

In another embodiment acetyl-carnitine is present in the culture medium of the present invention at a concentration from about 5 µM to about 15 µM.

In a preferred embodiment the acetyl-carnitine is present in the culture medium of the present invention at a concentration of about 10 µM.

In one embodiment lipoic acid or a derivative thereof is present in the culture medium of the present invention at a concentration of about 2.5 µM to about 20 µM, e.g. 5 µM to about 20 µM.

In another embodiment lipoic acid or a derivative thereof is present in the culture medium of the present invention at a concentration of about 2.5 µM to about 10 µM, e.g. 5 µM to about 10 µM.

In a preferred embodiment lipoic acid or a derivative thereof is present in the culture medium of the present invention at a concentration of about 5 µM.

In one embodiment acetyl-cysteine is present in the culture medium of the present invention at a concentration of about 5 to about 20 µM.

In another embodiment acetyl-cysteine is present in the culture medium of the present invention at a concentration of about 5 µM to about 15 µM.

In a preferred embodiment acetyl-cysteine is present in the culture medium of the present invention at a concentration of about 10 µM.

Suitably the medium according to the present invention may further comprise one or more additional compounds, e.g. an inorganic salt, an energy source, an amino acid, a protein source, a cytokine, a chelating agent, an antibiotic, a hyaluronan, a growth factor, a hormone, a vitamin and/or a granulocyte-macrophage colony-stimulating factor (GM-CSF).

In one embodiment the culture medium may comprise an inorganic salt. In one embodiment the inorganic salt may be one which dissociates into their inorganic ions in aqueous solution. Suitably the inorganic salt may be one which comprises one or more of the following inorganic ions: Na(+), K(+), Cl(−), Ca(2+), Mg(2+), SO(4)(2−), or PO(4)(2−).

In one embodiment the culture medium may comprise an energy source. The energy source may be pyruvate, lactate or glucose depending on the developmental stage of the embryo. Energy source requirements evolve from a pyruvate-lactate preference while the embryos, up to the 8-cell stage, are under maternal genetic control, to a glucose based metabolism after activation of the embryonic genome that supports their development from 8-cells to blastocysts. Suitably the one or more additional compounds may be or may include the carbohydrates lactate and pyruvate as an energy source.

In one embodiment the one or more additional compounds may be a hyaluronic acid. In one embodiment the culture medium may comprise an amino acid. The amino acid may be an essential amino acid. Suitably the essential amino acids include cysteine, histidine, isoleucine, leucine, lysine, methionine, valine, arginine, glutamine, phenylalanine, threonine and/or tryptophan. In an alternative embodiment the amino acid may be a non-essential amino acid, such as proline, serine, alanine, asparagine, aspartic acid, glycine and/or glutamic acid. Media that support the development of zygotes up to 8-cells may typically be supplemented with non-essential amino acids, such as proline, serine, alanine, asparagine, aspartic add, glycine and/or glutamic add. Media that support the development of 8-cell embryos up to the blastocyst stage are typically supplemented with essential amino acids, such cysteine, histidine, isoleucine, leucine, lysine, methionine, valine, arginine, glutamine, phenylalanine, threonine and/or tryptophan.

In one embodiment the culture medium may comprise a protein source. The protein source may be albumin or synthetic serum (e.g. at a concentration of 5 to 20% w/v or v/v respectively). Suitable sources for protein supplementation include human serum, human cord serum (HCS), human serum albumin (HSA), fetal calf serum (FCS) or bovine serum albumin (BSA).

In one embodiment the culture medium may comprise a growth factor.

In one embodiment the one or more additional compounds may be any compound present in a medium suitable for the culture of an embryo, a gamete or a stem cell.

Suitably the one or more additional compounds include a protein source, such as human serum albumin.

In one embodiment the one or more additional compounds may include water.

In one embodiment the one or more additional compounds may include a buffer solution. Suitable buffer solutions include HEPES buffer or MOPS buffer for example.

In one embodiment the one or more additional compounds may include water, inorganic salts, and at least one energy source.

In one embodiment the one or more additional compounds may include water, inorganic salts, at least one energy source, and one or more amino acids.

In one embodiment the one or more additional compounds may be or may comprise at least one energy source (e.g. a carbohydrate such as lactate, pyruvate), a protein source (e.g. human serum albumin), and water or a buffer solution.

In one embodiment the one or more additional compounds may be or may comprise an energy source (e.g. a carbohydrate such as lactate, pyruvate), an amino acid, hyaluronan and water or a buffer solution.

The one or more additional compounds may be in the form of a medium suitable for the culture of a gamete, an embryo or a stem cell, which medium could be referred to as a background medium.

The term "culture medium" as used herein is not limited to a medium for culturing (e.g. in conditions suitable for growth), but encompasses a medium using the handling or collection or manipulation of gametes, embryos and/or stem cells.

Suitably the one or more additional compounds may form a buffered medium (e.g. a bicarbonate buffered medium)

The one or more additional compounds may be in the form of a medium designed to support an embryo (e.g. a mammalian embryo) up to the 4-cell stage, which medium could be referred to as a background medium.

The one or more additional compounds may be in the form of a medium designed to support an embryo (e.g. a mammalian embryo) up to the 8-cell stage, which medium could be referred to as a background medium.

The one or more additional compounds may be in the form of a medium designed to support an embryo (e.g. a mammalian embryo) up to the blastocyst stage, which medium could be referred to as a background medium.

The (background) medium may be any medium suitable for the culture of an embryo, a gamete or a stem cell.

In one embodiment the (background) medium may be a medium specific for embryo transfer.

In one embodiment the (background) medium may be one or more of the group consisting of gamete handling medium (including gamete collection medium), a medium for intracytoplasmic sperm injection (ICSI), a fertilization medium, single step embryo culture medium, embryo transfer medium, oocyte maturation medium, sperm preparation and fertilisation medium, or any other suitable medium used for gametes or embryos.

In one embodiment the embryo culture medium or gamete culture medium according to the present invention may be one or more of the group consisting of a gamete handling medium (including gamete collection medium), a medium for intracytoplasmic sperm injection (ICSI), a fertilization medium, single step embryo culture medium, embryo transfer medium, oocyte maturation medium, sperm preparation and fertilisation medium, or any other suitable medium used for gametes or embryos.

In one embodiment the (background) medium may be any commercially-available simple culture medium, such as human tubal fluid (HTF), Whittingham's T6 medium and Earle's balanced salt solution (EBSS) (available from Irvine Scientific).

In one embodiment the (background) medium may be a basic medium such as IVF™ from Vitrolife. IVF™ may be considered a fertilisation media.

In one embodiment IVF media is considered to be a fertilisation media.

Alternatively or in addition the medium may be one or more of the following media G-1™, G-2™, HSA-Solution™, G-MOPS™ Plus, G-MOPS™, EmbryoGlue™, ICSI™ or G-TL™ or a combination thereof. These products are available from Vitrolife AB, Sweden. These could be referred to a background medium.

In one embodiment a suitable handling media (e.g. gamete handling media), may be G-MOPS™.

In one embodiment a suitable single step culture media may be G-TL™.

In one embodiment an embryo transfer media may be EmbryoGlue™. In some embodiments an embryo transfer media may be referred to as an implantation promoting transfer media.

In one embodiment the (background) media may be a medium such as oocyte maturation media or sperm preparation and fertilization media or a combination thereof.

The oocyte maturation media has been designed to provide improved development and survival of cultured oocytes. The complete formulation of a suitable oocyte maturation media is provided in the table below:

| Component | A<br>Most Preferred<br>Concentration | B<br>Preferred<br>Range |
| --- | --- | --- |
| NaCl | 90.08 | 80.0-100 |
| KCl | 5.5 | 3.5-7.5 |
| $NaH_2PO_4$ | 0.25 | 0.05-1.5 |
| $MgSO_4$ | 2 | 0.2-4.0 |
| $NaHCO_3$ | 25 | 15-30.0 |
| $CaCl_2$ | 1 | 0.8-2.8 |
| Glucose | 3.15 | 0.5-5.5 |
| NaLactate (L-isomer) | 5.87 | 2.0-20.0 |
| NaPyruvate | 0.1 | 0.01-1.0 |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Alanyl - Glutamine | 1 | 0.01-2.0 |
| Glycine | 0.1 | 0.01-0.5 |
| Proline | 0.1 | 0.01-0.5 |
| Serine | 0.1 | 0.01-0.5 |
| Cysteamine | 0.5 | 0.1-2.0 |
| L-Arginine-HCl | 0.6 | 0.1-1.2 |
| L-Cystine 2HCl | 0.1 | 0.05-0.25 |
| L-Histidine-HCl—H2O | 0.2 | 0.1-0.4 |
| L-Isoleucine | 0.4 | 0.1-0.8 |
| L-Leucine | 0.4 | 0.1-0.8 |
| L-Lysine-HCl | 0.4 | 0.1-0.8 |
| L-Methionine | 0.1 | 0.05-0.25 |
| L-Phenylalanine | 0.2 | 0.1-0.4 |
| L-Threonine | 0.4 | 0.1-0.8 |
| L-Tryptophan | 0.5 | 0.1-0.9 |

-continued

| Component | A<br>Most Preferred<br>Concentration | B<br>Preferred<br>Range |
|---|---|---|
| L-Tyrosine 2Na | 0.2 | 0.1-0.4 |
| L-Valine | 0.4 | 0.1-0.8 |
| D-Ca Pantothenate | 0.002 | 0.001-0.004 |
| Choline Chloride | 0.007 | 0.003-0.01 |
| Folic Acid | 0.0023 | 0.001-0.0045 |
| i-Inositol | 0.0111 | 0.005-0.02 |
| Niacinamide | 0.0082 | 0.004-0.016 |
| Pyridoxal HCl | 0.0049 | 0.002-0.01 |
| Riboflavin | 0.0003 | 0.0001-0.0006 |
| Thiamine HCl | 0.003 | 0.001-0.006 |
| HSA | 5 mg/ml | 1-10.0 mg/ml |
| Hyaluronate | 0.25 mg/ml | 0.05-0.5 mg/ml |
| ITS | 10 ng/ml | 1-100 ng/ml |
| IGF-I | 100 ng/ml | 10-1000 ng/ml |
| EGF | 100 ng/ml | 10-1000 ng/ml |
| FSH | 0.1 U/ml | 0.01-10 U/ml |
| hCG | 0.1 U/ml | 0.01-10 U/ml |

The concentrations in this table are provided in mM, unless otherwise indicated; the medium is aqueous.

The complete formulation of a suitable sperm preparation and fertilization media is provided in the table below:

| Component | A<br>Most Preferred<br>Concentration | B<br>Preferred<br>Range |
|---|---|---|
| NaCl | 100 | 75-100 |
| KCl | 5.5 | 3.5-7.5 |
| $NaH_2PO_4$ | 0.5 | 0.05-1.5 |
| $MgSO_4$ | 1 | 0.2-4.0 |
| Glucose | 3.15 | 0.5-5.6 |
| NaLactate (L-isomer) | 5 | 2.0-20 |
| NaPyruvate | 0.32 | 0.1-0.5 |
| $NaHCO_3$ | 25 | 15-30 |
| $CaCl_2$ | 1.8 | 0.8-2.8 |
| Glutathione | 1 mg/ml | 0.5-5.0 mg/ml |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Glycine | 0.1 | 0.01-0.5 |
| Proline | 0.1 | 0.01-0.5 |
| Serine | 0.1 | 0.01-0.5 |
| Taurine | 0.1 | 0.01-10.0 |
| HSA | 5 mg/ml | 1.0-10.0 mg/ml |
| Hyaluronate | 0.1 mg/ml | 0.02-0.5 mg/ml |
| Penicillin | 0.06 mg/ml | 0.01-0.1 mg/ml |
| Streptomycin | 0.05 mg/ml | 0.01-0.1 mg/ml |

The concentrations in this table are provided in mM, unless otherwise indicated; the medium is aqueous.

A medium for intracytoplasmic sperm injection (ICSI), e.g. ICSI™, is designed to aid sperm handling, facilitate sperm immobilization and injection into the oocyte during fertilization. The complete formulation for a suitable media for ICSI is provided in the table below:

| Component | A<br>Most Preferred<br>Concentration | B<br>Preferred<br>Range |
|---|---|---|
| NaCl | 90.08 | 75.0-105 |
| KCl | 5.5 | 3.5-7.5 |
| $MgSO_4$ | 2 | 0.4-4 |
| $NaHCO_3$ | 5 | 2.0-10 |
| MOPS/HEPES | 20 | 10-25.0 |
| $CaCl_2$ | 1 | 0.5-2.0 |
| NaLactate (L-isomer) | 10.5 | 5.0-20 |
| NaPyruvate | 0.32 | 0.1-1.0 |
| Alanyl - Glutamine | 0.5 | 0.1-2.0 |
| Glycine | 0.5 | 0.1-2.0 |
| Proline | 0.1 | 0.05-2.0 |
| Serine | 0.1 | 0.05-2.0 |
| Taurine | 0.1 | 0.05-5.0 |
| HSA | 5 mg/ml | 1-10.0 mg/ml |
| Hyaluronate | 0.1 mg/ml | 0.02-0.5 mg/ml |
| PVP | 10% | 1-20% |

The G1™ medium is designed to support the development of cleavage stage embryos to around the 8-cell stage. Such a medium contains carbohydrates, amino acids and chelators to support the early embryo. The complete formulation for the G-1™ medium is provided in the table below:

| Component | A<br>Most Preferred<br>Concentration | B<br>Preferred<br>Range |
|---|---|---|
| NaCl | 90.08 | 80.0-100 |
| KCl | 5.5 | 3.5-7.5 |
| $NaH_2PO_4$ | 0.25 | 0.05-1.5 |
| $MgSO_4$ | 1 | 0.2-2.0 |
| $NaHCO_3$ | 25 | 15.0-30 |
| $CaCl_2$ | 1.8 | 0.8-2.8 |
| Glucose | 0.5 | 0.05-5.0 |
| NaLactate (L-isomer) | 10.5 | 5.0-20 |
| NaPyruvate | 0.32 | 0.1-1.0 |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Alanyl - Glutamine | 0.5 | 0.1-1.0 |
| Glycine | 0.1 | 0.01-0.5 |
| Proline | 0.1 | 0.01-0.5 |
| Serine | 0.1 | 0.01-0.5 |
| Taurine | 0.1 | 0.01-10.0 |
| EDTA | 0.01 | 0.005-0.20 |
| HSA | 5 mg/ml | 1-10.0 mg/ml |
| Hyaluronate | 0.1 mg/ml | 0.02-0.5 mg/ml |

The concentrations in this table are provided in mM, unless otherwise indicated.

Alternatively, the (background) medium may be a commercially available IVF culture medium capable of supporting embryos beyond day 3 (8-cell stage). These culture media have been signed to carry embryos to the blastocyst stage prior to implantation. On example include α-modified essential medium (αMEM), described in Desai et al (Human Reprod. 12: 328-335 (1997)). A second example includes HECM-6 medium plus pantothenate (McKiernan S H & Bavister B D, Human Reprod. 15: 157-164 (2000). Other examples include G-2™ available from Vitrolife. G-2™ medium is designed to support the development of the embryo from around the 8-cell stage (day 3) to the blastocyst stage. Such a medium contains carbohydrates, amino acids and vitamins to support the later stage embryo.

The complete formulation for the G-2™ medium is provided in the table below:

| Component | A<br>Most Preferred<br>Concentration | B<br>Preferred<br>Range |
| --- | --- | --- |
| NaCl | 90.08 | 80.0-100 |
| KCl | 5.5 | 3.5-7.5 |
| NaH$_2$PO$_4$ | 0.25 | 0.05-1.5 |
| MgSO$_4$ | 1 | 0.2-4.0 |
| NaHCO$_3$ | 25 | 15-30.0 |
| CaCl$_2$ | 1.8 | 0.8-2.8 |
| Glucose | 3.15 | 0.5-5.5 |
| NaLactate (L-isomer) | 5.87 | 2.0-20.0 |
| NaPyruvate | 0.1 | 0.01-1.0 |
| Alanine | 0.1 | 0.01-0.5 |
| Asparate | 0.1 | 0.01-0.5 |
| Asparagine | 0.1 | 0.01-0.5 |
| Glutamate | 0.1 | 0.01-0.5 |
| Alanyl - Glutamine | 1 | 0.01-2.0 |
| Glycine | 0.1 | 0.01-0.5 |
| Proline | 0.1 | 0.01-0.5 |
| Serine | 0.1 | 0.01-0.5 |
| L-Arginine-HCl | 0.6 | 0.1-1.2 |
| L-Cystine 2HCl | 0.1 | 0.05-0.25 |
| L-Histidine-HCl—H2O | 0.2 | 0.1-0.4 |
| L-Isoleucine | 0.4 | 0.1-0.8 |
| L-Leucine | 0.4 | 0.1-0.8 |
| L-Lysine-HCl | 0.4 | 0.1-0.8 |
| L-Methionine | 0.1 | 0.05-0.25 |
| L-Phenylalanine | 0.2 | 0.1-0.4 |
| L-Threonine | 0.4 | 0.1-0.8 |
| L-Tryptophan | 0.5 | 0 1-0.9 |
| L-Tyrosine 2Na | 0.2 | 0.1-0.4 |
| L-Valine | 0.4 | 0.1-0.8 |
| D-Ca Pantothenate | 0.002 | 0.001-0.004 |
| Choline Chloride | 0.007 | 0.003-0.01 |
| Folic Acid | 0.0023 | 0.001-0.0045 |
| i-Inositol | 0.0111 | 0.005-0.02 |
| Niacinamide | 0.0082 | 0.004-0.016 |
| Pyridoxal HCl | 0.0049 | 0.002-0.01 |
| Riboflavin | 0.0003 | 0.0001-0.0006 |
| Thiamine HCl | 0.003 | 0.001-0.006 |
| HSA | 5 mg/ml | 1-10 mg/ml |
| Hyaluronate | 0.1 mg/ml | 0.02-0.5 mg/ml |

The concentrations in the above table are provided in mM, unless otherwise indicated.

In one embodiment, 8-cell stage embryos are transferred from an embryo culture medium optimized to support early stage growth (i.e. up to the 8-cell stage) supplemented in accordance with the present invention to an embryo culture medium optimized to support later stage growth (i.e. up to the blastocyst stage)—which may be further supplement in accordance with the present invention.

The concentration of each compound in a culture medium may vary depending upon the stage of embryo development for which the medium is optimised. Typical concentrations for the inorganic salts in the culture medium may be about 100 mM to about 150 mM or about 110 mM to about 140 mM.

Typical concentrations for the energy source in the media may be about 5 mM to about 40 mM, e.g. about 5 mM to about 30 mM, or about 5 mM to about 15 mM.

Typical concentrations for the total amount of amino acids in the culture media may be about 0.1 mM to about 15 mM or about 0.5 mM to about 12 mM, or about 0.5 mM to about 6 mM. The vitamins, growth factors, hormones and other miscellaneous ingredients in the culture medium tend to be added at fairly low concentrations, e.g. 1 mM or less, 0.5 mM or less or even 0.1 mM or less.

Preferably the embryo, gamete or stem cell is cultured under paraffin oil. This can prevent evaporation of the medium and thus preserving a constant osmolarity. In addition the oil may minimize fluctuations of pH and temperature.

In one embodiment the culture medium of the present invention may comprise an antibiotic. Some examples of suitably antibiotics include penicillin and streptomycin.

In one embodiment the present invention provides a method for handling and/or manipulating and/or culturing an embryo and a gamete the method comprising handling and/or manipulating and/or culturing the embryo and gamete in a culture medium according to the present invention.

The present invention includes using a combination of acetyl-carnitine (e.g. at a concentration of 5-50 μM) and lipoic acid or a derivative thereof (e.g. at a concentration of about 2.5 to about 40 μM) and optionally acetyl-cysteine (e.g. at a concentration of about 5 to about 50 μM) during both gamete handling (e.g. in gamete handling medium (including gamete collection medium), in sperm preparation medium, in oocyte maturation medium or any other suitable medium used for gametes) and embryo manipulation (e.g. in a medium for intracytoplasmic sperm injection (ICSI), a fertilization medium, single step embryo culture medium, embryo transfer medium, or any other suitable medium used for embryos).

In one embodiment the present invention relates to the use of a combination of acetyl-carnitine (e.g. at a concentration of 5-50 μM) and lipoic acid or a derivative thereof (e.g. at a concentration of about 2.5 to about 40 μM) and optionally acetyl-cysteine (e.g. at a concentration of about 5 to about 50 μM) during both gamete handling (e.g. in gamete collection medium) and during embryo manipulation, such as during ICSI or fertilization or embryo transfer (e.g. in a medium for intracytoplasmic sperm injection (ICSI) or in a fertilization medium or an embryo transfer medium).

In one embodiment the present invention relates to the use of a combination of acetyl-carnitine (e.g. at a concentration of 5-50 μM) and lipoic acid or a derivative thereof (e.g. at a concentration of about 2.5 to about 40 μM) and optionally acetyl-cysteine (e.g. at a concentration of about 5 to about 50 μM) in an embryo culture medium.

In some embodiments the compounds for use in the present invention are added during gamete handling and/or during embryo manipulation and/or during embryo culture. In other words the compounds for use in the present invention may be added at multiple stages during the IVF/ICSI process.

In some embodiments the compounds for use in the present invention are added to the gamete handling medium and/or the embryo manipulation medium and/or the embryo culture medium.

The term "handling" as used herein may include any holding or moving, e.g. of the gamete, embryo or stem cell. For example this may include transfer of gametes during and after collection or transferring embryos for implantation.

The term "manipulation" as used herein may include any manipulation of the gamete and/or embryo and/or stem cell. For example this may include ICSI or fertilisation (e.g. by letting the sperm fertilise the ovum).

The term "culture" as used herein may mean maintaining in conditions suitable for growth or maturation.

Preferably the pH of the culture medium is (maintained at) between 7.2 to 7.4 (during culture).

It has surprisingly been found that the culture medium according to the present invention reduces or prevents oxidative stress and/or reduces or prevents free-radical formation (e.g. reactive oxygen species (ROS) formation)

and/or increases levels of antioxidant capacity in a gamete, an embryo or a stem cell cultured in vitro.

Oxidative stress reflects an imbalance between the systemic manifestation of reactive oxygen species and the embryo's or stem cell's ability to readily detoxify the reactive intermediates or to repair the resulting damage. Disturbances in the normal redox state of cells can cause toxic effects through the production of peroxides and free radicals that damage all components of the cell, including proteins, lipids and DNA. Oxidative stress from oxidative metabolism causes base damage, as well as strand breaks in DNA. Base damage is mostly indirect and caused by reactive oxygen species (ROS) generated, e.g. O2- (superoxide radical), OH (hydroxyl radical) and H2O2 (hydrogen peroxide). Further, some reactive oxidative species act as cellular messengers in redox signaling. Thus, oxidative stress can cause disruptions in normal mechanisms of cellular signaling.

The term "antioxidant capacity" as used herein means is the ability of the embryo or stem cell to tolerate oxidative stress. Antioxidant capacity of an embryo can be measured indirectly by measuring growth rate of the embryo and/or by measuring intracellular glutathione (GSH) (as detailed in the methods and materials section below).

In one embodiment the culture medium according to the present invention maintains the levels of GSH within the in vitro cultured embryos at levels substantially the same as those of in vivo developed embryos. In other words, the specific combinations of acetyl-carnitine, lipoic acid and (optionally) acetyl-cysteine taught herein in a culture medium according to the present invention increases GSH levels in in vitro cultured embryos compared with embryos cultured in vitro in a culture medium without this combination of compounds.

Without wishing to be bound by theory GSH is a sulphydryl thiol peptide, which plays a critical role in protecting cells from oxidative damage. Its role in embryo development has been demonstrated in cell proliferation and progression during embryonic events. GSH synthesis is dependent on the availability of cysteine, and due to feedback inhibition, intracellular levels of cysteine determine the upper concentration of cellular GSH. Therefore, an increase in GSH may protect the cell from oxidative stress due to a greater antioxidant capacity thus facilitating improved embryo quality.

Growth rate can be measured by measuring the trophectoderm cell number, inner cell mass number, or total cell number, for example at 2 days of culturing in a culture media of the present invention or at the blastocyst stage, e.g. suitably when measured at 5 days of culturing in a culture media of the present invention; by measuring time to reach expanded blastocyst; and/or by measuring time to reach hatching blastocyst.

Additionally or alternatively it has surprisingly been found that the culture medium according to the present invention improves the development of an embryo cultured in vitro.

The term "improves the development" in relation to an embryo as used herein may include one or more of the following:
a) increasing trophectoderm cell number in the embryo at the blastocyst stage, e.g. when measured at 5 to 6 days of culturing in a culture media of the present invention);
b) increasing inner cell mass in the embryo at the blastocyst stage, e.g. when measured at 5 to 6 days of culturing in a culture media of the present invention;
c) increasing total cell number in the embryo at the blastocyst stage, e.g. when measured at 5-6 days of culturing in a culture media of the present invention);
d) a reduced time to reach expanded blastocyst;
e) a reduced time to reach hatching blastocyst;
f) an increase in fetal weight after embryo transfer;
g) an increase in fetal crown-rump length after embryo transfer;
h) an increase in placental weight after embryo transfer;
i) an increase in good quality blastocysts (GQB) (i.e. the fraction of blastocysts that reached a score of 3AB or higher according to the Gardner blastocyst grading system, (see Gardner et al 1999) per total number of blastocysts compared with embryos cultured in comparable media without antioxidants; and/or
j) an increase in blastocyst utilization rate (i.e. the fraction of blastocysts that are either used fresh for transfer or cryopreserved for later transfer to the patient, e.g. in percent of total number of fertilised oocytes or in percent of total number of blastocysts.

The term "inner cell mass (ICM)" is herein defined is the mass of cells inside the embryo that will eventually give rise to the definitive structures of the fetus. Inner cell mass may be also known as the embryoblast or pluriblast.

The term "trophectoderm (TE)" is herein defined as the cells forming the outer layer of a blastocyst, e.g. which provide nutrients to the embryo and develop into a large part of the placenta.

The term "expanded blastocyst" as used herein means the developmental stage when the blastocoel cavity is larger than the embryo. Typically this is in combination with the thinning of the blastocyst shell (zona pellucida).

The term "hatching blastocyst" as used herein means the point when the embryo frees itself from the enveloping pellucid zone. Through a series of expansion-contraction cycles the embryo bursts the covering. This is supported by enzymes that dissolve the pellucid zone at the abembryonic pole. The rhythmic expansions and contractions result in the embryo herniating out of and emerging from the rigid glycoprotein coat (zona pellucida).

The term "improves" (e.g. in relation to development and/or proliferation and/or differentiation) means improves compared with a control (e.g. grown in a similar culture medium, but without the combination of acetyl-carnitine and lipoic acid or a derivative thereof or the combination of acetyl-carnitine and lipoic acid or a derivative thereof and acetyl-cysteine as defined in the present invention).

In a preferred embodiment the embryo is a mammalian embryo, e.g. a human embryo.

In one embodiment the embryo is a human embryo.

The preimplantation period of embryo development varies between mammalian species. However, the embryos of humans and mice share the most similar length of development (around 4 to 5 days) and also exhibit quite similar implantation. The blastocysts of both species reach a similar size and the nutrient utilization patterns are very similar between mice the embryos of humans and mice (see for example Gott A L, Hardy K, Winston R M, Leese H J. Non-invasive measurement of pyruvate and glucose uptake and lactate production by single human preimplantation embryos. Hum Reprod. 1990; 5(1):104-8; Leese H J, Barton A M. Pyruvate and glucose uptake by mouse ova and preimplantation embryos. J Reprod Fertil. 1984; 72(1):9-13; and Gardner D K, Wale P L. Analysis of metabolism to select viable human embryos for transfer. Fertility and Sterility. 2013; 99(4):1062-72). The similarities shared between human and mouse development are such that they allow for the evaluation of human development from experiments performed on murine systems (see Csaba Pribensky et al. Reproductive Biomedicine Online (2010) 20, 371-379). Consequently, it is held that the mouse makes the most appropriate model for the human preimplantation embryo.

The term "gamete" as used herein can refer to an oocyte cell and/or a sperm cell.

The term "embryo" as used herein may have a broad definition, which includes the pre-embryo phase. The term "embryo" as used herein may encompass all developmental stages from the fertilization of the oocyte through compaction, morula, blastocyst stages, hatching and implantation.

In some cases the term "embryo" is used to describe a fertilized oocyte after implantation in the uterus until 8 weeks after fertilization at which stage it become a fetus in humans. According to this definition the fertilized oocyte is often called a pre-embryo until implantation occurs. However as noted above the term "embryo" as used herein may include the pre-embryo phase.

An embryo is approximately spherical and is composed of one or more cells (blastomeres) surrounded by the acellular matrix known as the zona pellucida. The zona pellucida performs a variety of functions until the embryo hatches, and is a good landmark for embryo evaluation. The zona pellucida is spherical and translucent, and should be clearly distinguishable from cellular debris.

Fertilization is the time point where the sperm cell is recognized and accepted by the oocyte. The sperm cell triggers egg activation after the meiotic cycle of the oocyte has been suspended in metaphase of the second meiotic division. This results in the production and extrusion of the second polar body. This is the time point referred to herein as the second polar body excluding (see reference value ii.). Some hours after fusion of sperm and ovum, DNA synthesis begins. Male and female pronuclei (PN) appear. This is the time point referred to as when the pronuclei (PN) appear (see reference value iii.). The PN move to the centre of the egg and the membranes breakdown and the PN disappear. This is the time point referred to herein as the time point when the pro-nuclei have disappeared (or faded) (see reference value i.). This combination of the two genomes is called syngamy. Hereafter, the cell divisions begin.

During embryonic development, blastomere numbers increase geometrically (1-2-4-8-16- etc.). Synchronous cell cleavage is generally maintained to the 8-cell stage in human embryos. After that, cell cleavage becomes asynchronous and finally individual cells possess their own cell cycle. Human embryos produced during infertility treatment are usually transferred to the recipient before 8-blastomere stage. In some cases human embryos are also cultivated to the blastocyst stage before transfer. This is preferably done when many good quality embryos are available or prolonged incubation is necessary to await the result of a pre-implantation genetic diagnosis (PGD). However, there is a tendency towards prolonged incubation as the incubation technology improves.

Accordingly, the term embryo is used in the following to denote each of the stages fertilized oocyte, zygote, 2-cell, 4-cell, 8-cell, 16-cell, compaction, morula, blastocyst, expanded blastocyst and hatched blastocyst, as well as all stages in between (e.g. 3-cell or 5-cell).

An embryo is formed when an oocyte is fertilized by fusion or injection of a sperm cell (spermatozoa). The term is traditionally used also after hatching (i.e. rupture of zona pelucida) and the ensuing implantation. For humans the fertilized oocyte is traditionally called a zygote or an embryo for the first 8 weeks. After that (i.e. after eight weeks and when all major organs have been formed) it is called a fetus. However the distinction between zygote, embryo and fetus is not generally well defined. The terms embryo and zygote are used herein interchangeably.

In one embodiment, the embryo may be cultured individually.

In yet another embodiment, the embryo is cultured in the culture medium of the present invention until the blastocyst stage, expanded blastocyst stage or hatched blastocyst stage.

Additionally or alternatively it has surprisingly been found that the culture medium according to the present invention improves the proliferation and differentiation of a stem cell cultured in vitro. The term "differentiation" as used herein (e.g. in relation to stem cell development) means the process by which a cell changes from one cell type to another. This term may encompass a less specialized cell type becoming a more specialized cell type, such as during cell growth.

The term "proliferation" as used herein (e.g. in relation to stem cell development) means the multiplication of stem cells, e.g. resulting in the expansion of the stem cell population.

The term "stem cell" as used herein means undifferentiated biological cells that can differentiate into specialized cells and can divide (through mitosis) to produce more stem cells. The term "stem cell" encompasses both embryonic stem cells, which may be isolated from the inner cell mass of blastocysts, and adult stem cells, which may be found in various tissues. In addition or alternatively, the term "stem cell" as used herein means an induced pluripotent stem cell (iPSC). iPSCs are a type of pluripotent stem cell that can be generated directed from adult cells.

In one embodiment the term stem cell means embryonic stem cell.

Notably embryonic stem cells are derived from the inner cell mass of an embryo. The inventors of the present invention have shown that the culture medium of the present invention protects and/or improves the development of the inner cell mass. Thus the culture medium of the present invention protects embryonic stem cells, which are derived from the inner cell mass.

In one embodiment the stem cell may be a human stem cell.

In one embodiment the (background) medium may be a medium specific for stem cell culture. Any known stem cell culture medium may be used as the background medium.

In one embodiment the stem cell (background) medium may be a media for the culture of a pluripotent stem cell.

In one embodiment the stem cell (background) medium may be a media for the culture of human embryonic stems cells and/or iPS cells.

In one embodiment the stem cell (background) medium may be the commercially available medium known as mTeSR™1, e.g a defined, feeder-free maintenance medium for human embryonic stem cells and iPS cells (available from StemCell™ Technologies, UK.

The embryo or stem cell may be cultured in an environment with an oxygen content of between 5-20% v/v.

In one embodiment the embryo, gamete or stem cell is cultured under ambient oxygen conditions. Ambient oxygen conditions as used herein may be between about 18-22% v/v or between about 19-21% v/v. In one embodiment the ambient oxygen conditions are about 20% v/v.

In another embodiment the embryo, gamete or stem cell is cultured under reduced oxygen conditions. Reduced oxygen conditions as used herein may be a concentration of oxygen between about 3% (v/v) to about 7% (v/v) or between about 4% (v/v) to about 6% (v/v). In one embodiment the reduced oxygen conditions are about 5% (v/v).

The present invention relates to the use of lipoic acid or a derivative thereof. The term lipoic acid may mean α-lipoic acid. This compound can be any racemic form e.g. (±)-1,2-Dithiolane-3-pentanoic acid, (R)-5-(1,2-dithiolane-3-yl) pentanoic acid or (S)-1,2-Dithiolane-3-pentanoic acid. The lipoic acid or derivative thereof may be added as a mixture of enantiomeric forms, or as a single enantiomer. In the latter case, the R-enantiomer has been found to be more biologically active. One derivative of lipoic acid for use in the present invention is lipoate. Lipoate is a salt or ester derivative of lipoic acid. A further derivative of lipoic acid includes methylated lipoic acid. The term "derivative" as used herein in relation to lipoic acid means biologically active amphiphilic disulfide/thiotic molecules that have essentially equivalent physiological properties as lipoic acid.

The term "acetyl-cysteine" as used herein may be N-acetyl-L-cysteine (NAC) (e.g. unmodified NAC), or a derivative thereof, such as N-acetylcysteine-amide (NACA).

In a preferred embodiment the term "acetyl-cysteine" as used herein means N-acetyl-L-cysteine (NAC) (e.g. unmodified NAC).

The term acetyl-carnitine may be referred to as acetyl-L-carnitine.

In one embodiment the embryo or stem cell may be cultured in the medium of the present invention at a temperature of between about 35° C. to about 39° C.

In a preferred embodiment the embryo or stem cell may be cultured in the medium of the present invention at a temperature between about 36.5° C. to about 37.5° C.

In a most preferable embodiment the embryo or stem cell may be cultured in the medium of the present invention at a temperature of about 37° C.

In one embodiment the culture medium according to the present invention does not comprise co-enzyme Q or ubiquinone.

In one embodiment the culture medium according to the present invention does not comprise co-enzyme Q or ubiquinone in the region of 0.0001% to 0.005% by weight in the final composition.

In one embodiment the culture medium according to the present invention does not comprise a polysorbate surfactant. The polysorbate surfactant may be for example Tween™ or Span™.

A reference to a gamete as referred to herein include both a singular gamete and multiple gametes. In other word a gamete means "a gamete or gametes".

A reference to an embryo as referred to herein include both a singular embryo and multiple embryos. In other word an embryo means "an embryo or embryos".

A reference to a stem cell as referred to herein include both a singular stem cell and multiple stem cells. In other word a stem cell means "a stem cell or stem cells".

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an embryo" includes a plurality of such candidate embryos, and so forth.

The publications discussed herein are provided solely for their disclosure prior to the filing date of the present application. Nothing herein is to be construed as an admission that such publications constitute prior art to the claims appended hereto.

All patent and non-patent references cited in the application, or in the present application, are also hereby incorporated by reference in their entirety.

The invention will now be described, by way of example only, with reference to the following Figures and Examples.

EXAMPLES

Methods and Materials
Embryo Collection

F1 virgin hybrid female mice (C57BL/6×CBA) at 3-4 weeks old were intraperitoneally injected with 5 IU of pregnant mare's serum gonadotrophin. 48 hours later 5 IU of human chorulon gonadotrophin was administered and the female mice mated with F1 male mice >12 weeks old. Successful mating was confirmed by the presence of a vaginal mucus plug the following morning. Pronucleate oocytes were collected 22 hours after hCG injection, in pre-warmed handling medium (G-MOPS) supplemented with 5 mg/ml human sera albumin. Cumulus cells were denuded from the oocytes with GMOPS containing 300 IU/ml hyaluronidase. All embryos were washed twice in G-MOPS media and once in G-1™ medium prior to allocation for culture. Animals were housed in 12 hour light-day photoperiod with food and water available ad libitum. All mice experimentation was approved by the Institutional Animal Ethics Committee.

Embryo Culture

Embryos were cultured in groups of 10 in 20 ul drops of media under paraffin oil in 6% $CO_2$ in air (atmospheric oxygen ~20%) or at 6% $CO_2$ 5% oxygen at 37° C. in a humidified multi gas incubator (Sanyo MCOK-5M[RC], Japan). Embryos were cultured in G-1™ medium (G-1™ with HSA-Solution™, Vitrolife) for 48 hours and then for a further 48 hours in G-2™ medium (G-2™ with HSA-Solution™, Vitrolife). Blastocysts chosen for uterine transfer on day 4 were cultured in G2 medium for 24 hours prior to transfer. All cultures were performed in 35 mm petri dishes (Falcon, BD Biosciences).

Embryo Transfer

F1 female mice 8-12 weeks of age were mated with vasectomised males to establish pseudopregnancy. Successful mating was confirmed by the presence of a vaginal plug the following morning. Day 4 blastocysts (96 hours post insemination) were transferred surgically to the uterus of day 4 pseudopregnant female mice (synchronous to recipient female reproductive tract). Recipient female mice were anesthetised with isoflurane gas. Five embryos were transferred with a glass pipette through a dorsal incision, into the lumen of each uterine horn, with each recipient female receiving embryos from control and treatment groups. To avoid any preferential implantation bias, alternate groups were transferred to both the right and left horn per recipient. Following embryo transfer, the skin wound was sealed with sterile surgical clips. Pregnant females were sacrificed 10 days later and foetus development or resorption sites recorded. Measurements were taken of the crown-rump length, fetal and placental weights and morphological grades of fetal ear, eye and limb development were determined as devised by Wahlsten and Wainwright (1977) (J. of Embryology and Experimental Morphology 42: 79-92), which reference is herein incorporated by reference.

Determination of Embryo Cell Numbers

Differential staining of embryos was performed by techniques commonly known in the art to determine the allocation of cells to the inner cell mass (ICM) and trophectoderm (TE) on day 5 (e.g. in the blastocyst). Briefly, after zona removal using pronase, embryos were treated with a complement reaction which labels the in TE nuclei with propidium iodide and leaves the ICM intact and unlabelled. Following bisbenzimide treatment, all nuclei were stained. Embryos were whole-mounted in glycerol and imaged using an inverted fluorescence microscope (Nikon Eclipse TS100) fitted with a digital camera (Nikon digital sight DS-Fi1) and nuclei counted using imaging software ImageJ.

Embryo Culture for MCB and BSO Treatment

Embryos were cultured in groups of 10 in 20 ul drops of media under paraffin oil (Ovoil, Vitrolife) in 6% $CO_2$, 20% $O_2$ 74% $N_2$ at 37° C. in a humidified multi gas incubator (Sanyo MCOK-5M[RC], Japan). Half of the embryos were allocated to the control group and the other half to the treatment group. Control group embryos were cultured in G-1™ medium (G-1™ with HSA-Solution™, Vitrolife) for 4 hours. Treatment group embryos were likewise cultured with the optimal triple antioxidant dose supplemented in the G-1™ medium (as determined in Example 2).

BSO Dosage Optimization

Immediately after collection, pronucleate control embryos were incubated in G-1™ medium spiked with BSO at doses of 0, 50, 100, 200, 400, 800, 1600 µM for 4 hours at 6% $CO_2$, 20% $O_2$ 74% $N_2$ at 37° C. Embryos were rinsed thoroughly in G-1™ with HSA-Solution™ media and placed individually in 2 µl drops of GMOPS with HSA-Solution™ (G-MOPS™ Plus, Vitrolife AB, Sweden) made on glass bottom dishes (Fluorodish, Coherent Scientific, Australia) and overlayed with paraffin oil (Ovoil, Vitrolife) for fluorescence imaging. Optimal dosage was determined by recording the fluorescence at 360±40 nm/460±40 nm excitation/emission wavelengths under a fluorescence microscope (Nikon Eclipse TS100). Results were calculated by subtracting the values of blank (embryos with no BSO exposure) and basal levels of the culture media from the fluorescence recorded. All media and oil used were pre-equilibrated overnight at 6% $CO_2$, 20% $O_2$ 74% $N_2$ at 37° C.

MCB Dosage Optimization

MCB fluorescent probe optimisation was carried out similarly to the BSO optimisation as previously described with embryos incubated in G-1™ medium supplemented with MCB at doses of 0, 1.25, 2.5, 5, 10, 20, 40, 80, 160, 320, 640 µM for 15 minutes.

Verification of MCB Specificity to Glutathione (GSH)

The optimal doses of 200 µM BSO and 10 µM MCB were used to verify the specificity of MCB to GSH. Verification was carried out in the same way as the probe dosage optimisations as previously described. Immediately after collection pronucleate embryos were incubated in G-1™ medium supplemented with 200 µM BSO for 4 hours. Following thorough rinsing in G-1™ with HSA-Solution™ media, embryos were further cultured in 10 µM MCB for 15 minutes. After a final thorough rinse in G-1™ with HSA-Solution™, embryos were placed individually in 2 µl drops of G-MOPS™ with HSA-Solution™ under paraffin oil and fluorescence images taken.

Determination of Glutathione Levels 4 hours following oocyte collection and incubation, embryos from both control and treatment groups were treated with 10 µM MCB for 15 minutes under the same culture conditions. After embryos were rinsed and placed in individual 2 ul G-1™ media drops, fluorescence was captured as previously described. To assess the time course of MCB images were taken every 10 minutes.

Statistical Analysis

Cell number data for all treatments compared to the control were subjected to a one-way analysis of variance (ANOVA) followed by Bonferroni multiple comparisons test. Proportion data were compared using a 3×2 contingency table. For single doses, data means were compared to controls using Student's t-test. All groups were tested for normality prior to analysis using Bartlett's test. Differences were considered biologically significant at a P-value of 0.05. All the analyses were performed using GraphPad Prism version 5.04 for Windows (obtainable from GraphPad Software).

Example 1: Group Embryo Development in 20% $O_2$ with Single Compounds

Figure 1B:
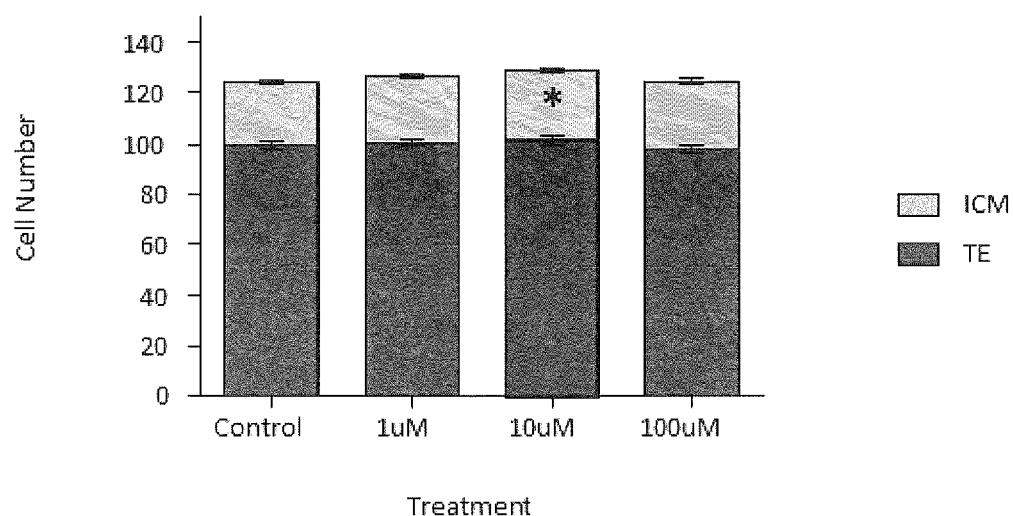
FIG. 1b shows group embryo development in 20% oxygen with acetyl cysteine at different dosages.
Figure 1C:
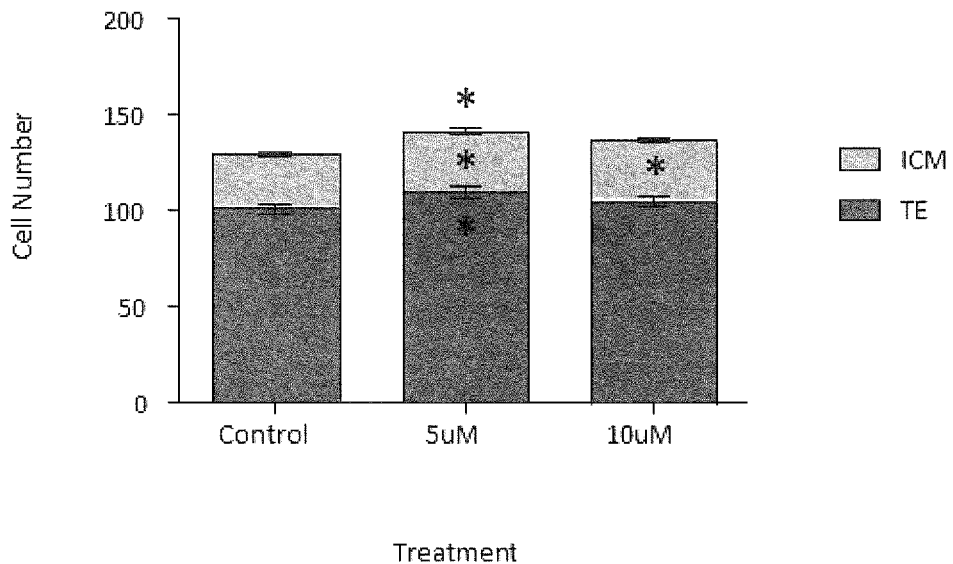
FIG. 1c shows group embryo development in 20% oxygen with lipoic acid at different dosages.

Embryos cultured in control groups were grown in G-™1 and G-2™ medium supplemented with HSA 5 mg/ml (HSA, Vitrolife). Embryos in treatment groups were similarly cultured with Acetyl Carnitine, Acetyl Cysteine or α-Lipoic acid Sigma Aldrich, USA) supplemented in the G-1™ and G-2™ medium at doses of 1, 10 and 100 µM and supplemented with HSA as the control group. The optimal dose for carnitine (FIG. 1a and Table 1a which represent two independent experiments), cysteine (FIG. 1b and Table 1b which represent two independent experiments) and lipoic acid (FIG. 1c and Table 1c) were determined by culturing embryos and analysing resultant blastocyst cell lineage numbers. The "total mean" means the average total number of cells in the embryo (including inner cell mass and trophectoderm) at day 5. The dose that resulted in significantly higher cell numbers was deemed the optimal dose. The optimal dose for acetyl carnitine was found to be 10 µM with significantly increased trophectoderm cells resulting in increased blastocyst cell number. Similarly the optimal dose for acetyl cysteine was 10 µM with significantly increased blastocyst inner cell number. 5 µM was found to be the optimal dose for lipoic acid showing significantly higher trophectoderm and inner cell numbers resulting in increased blastocyst cell number. There was no negative effect on any treatments on the blastocyst formation compared with control (data not shown).

TABLE 1a

| Treatment | No. Embryos | Total Mean |
|---|---|---|
| Control | 11 | 90.09 |
| 1 μM | 13 | 95.85 |
| 10 μM | 11 | 107.83 |
| 30 μM | 14 | 86.93 |
| 1000 μM | 17 | 67.41 |

TABLE 1b

| Treatment | No. Embryos | Total Mean |
|---|---|---|
| Control | 12 | 93.75 |
| 1 μM | 12 | 81.92 |
| 10 μM | 7 | 109.29 |
| 30 μM | 8 | 104.38 |
| 1000 μM | 12 | 95.17 |

TABLE 1c

| Treatment | No. Embryos | Total Mean |
|---|---|---|
| Control | 66 | 80.2 |
| 5 μM | 62 | 90.2 |
| 10 μM | 62 | 91.3 |
| 20 μM | 63 | 94 |
| 80 μM | 65 | 34.0 |

In addition these data show that solely raising the concentration of a single compound does not bring the benefits associated with the combinations of the present invention.

Example 2: Effect of Combined Antioxidants on Blastocyst Cell Number

Figure 2:
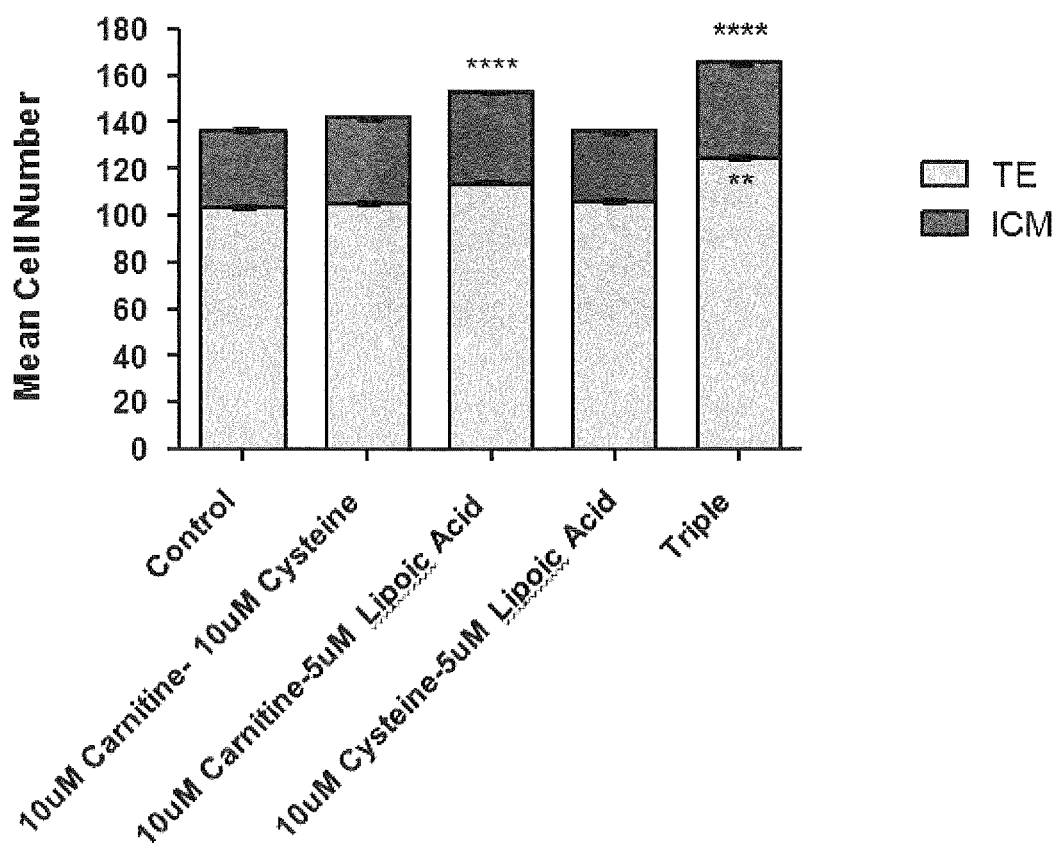
FIG. 2 shows cell lineage allocation of embryos cultured in 20% 02. Data are expressed as mean±SEM. Light and dark bar portions represent the average TE and ICM cells respectively. Control (n=35), 10 µM Carnitine-10 µM Cysteine (n=42), 10 µM Carnitine-5 uM lipoic acid (n=53), 10 µM Cysteine-5 uM lipoic acid (n=48), Triple (10 µM Carnitine-10 µM Cysteine-5 µM lipoic acid) (n=44). 3 biological replicates. P<0.01, **P<0.0001.

Embryos cultured in control groups were grown in G-1™ and G-2™ medium supplemented with HSA-Solution™ 5 mg/ml. Embryos in treatment groups were similarly cultured with 10 μM Acetyl Carnitine-10 μM Acetyl Cysteine, 10 μM Acetyl Carnitine-5 μM Lipoic acid, 10 μM Acetyl Cysteine-5 μM Lipoic acid, the triple cocktail of 10 μM Acetyl Carnitine-10 μM Acetyl Cysteine 5 μM Lipoic acid supplemented in the G-1™ and G-2™ medium and supplemented with HSA. Blastocyst cell number after 5 days of incubation was significantly higher in embryos treated with the triple antioxidant cocktail than double antioxidants treatments. While the 10 uM Carnitine-5 uM lipoic acid group also had significantly higher total cell numbers compared to the control, the triple cocktail also had significantly increased TE cells that contributed to higher total cell number (FIG. 2).

Example 3: Group Embryo Development in 5% $O_2$ with Combined Compounds

Figure 3:
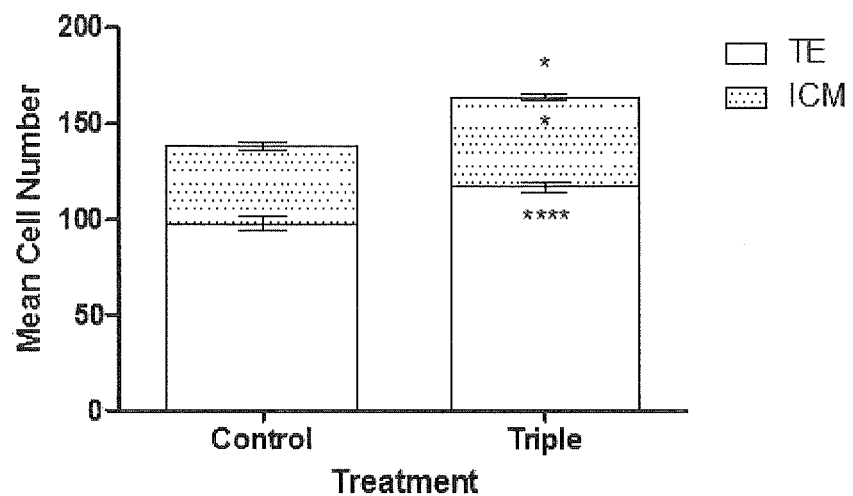
FIG. 3 shows cell lineage allocation of embryos cultured groups in 5% 02. Cocktail comprising of 10 µM Carnitine, 10 µM Cysteine and 5 µM lipoic acid. Data are expressed as mean±SEM. Light and dark bar portions represent the average TE and ICM cells respectively. 3 biological replicates. Control (n=154), Cocktail (n=168). ***P<0.005, *P<0.05.

Embryos were cultured in groups of 10 in 20 μl drops of media under paraffin oil (Ovoil, Vitrolife) in 6% $CO_2$, 5% $O_2$ 89% $N_2$ at 37° C. in a humidified multi gas incubator (Sanyo MCOK-5M[RC], Japan). Half of the embryos were allocated to the control group and the other half to the treatment group. Treatment group embryos were cultured with the optimal antioxidant dose supplemented in the medium, as determined previously. When cultured at 5% $O_2$, embryos cultured individually with the triple cocktail had significantly increased ICM and trophectoderm cells resulting in increased blastocyst total cell number (FIG. 3).

Example 4: Individual Embryo Culture in 20% 02 with Combined Compounds

Figure 4:
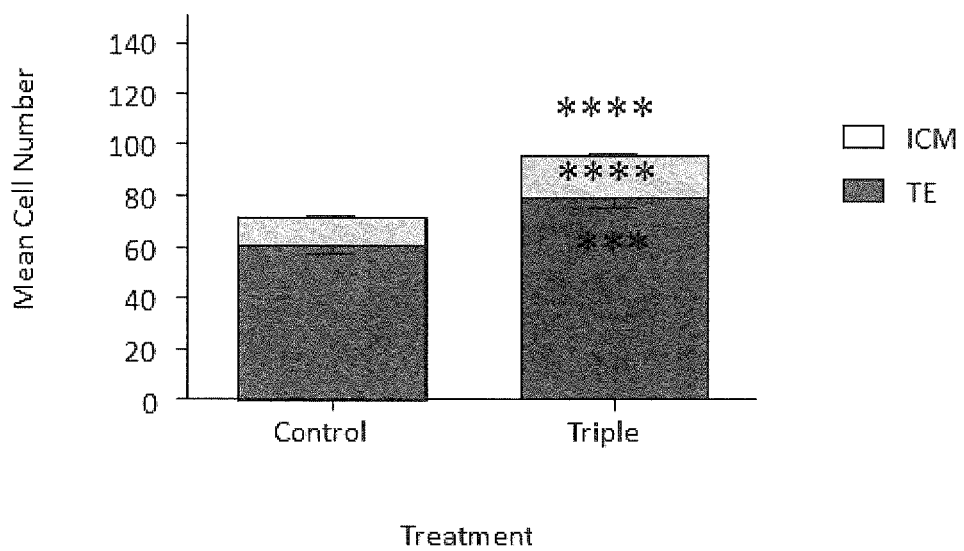
FIG. 4 shows cell lineage allocation of embryos cultured individually in 20% 02. Data are expressed as mean±SEM. Light and dark bar portions represent the average TE and ICM cells respectively. 6 biological replicates. Control (n=116), Cocktail (n=145). **P<0.0001, *P<0.005.

Embryos were cultured individually in 20 μl drops of media under paraffin oil in 6% CO2 in air (atmospheric oxygen ~20%) at 37° C. in a humidified multi gas incubator (Sanyo MCOK-5M[RC], Japan). Half of the embryos were allocated to the control group and the other half to the treatment group. Embryos cultured individually with the triple cocktail had significantly increased ICM and trophectoderm cells resulting in increased blastocyst total cell number (FIG. 4). These results showing that the improved embryo development is also observed during individual culturing. While total cell numbers were lower in individually cultured embryos, the effects of combining the antioxidants were greater for embryos cultured individually as opposed to cultured in groups, with increased ICM, TE and total cell number (FIG. 4 vs. FIG. 2).

Figure 5:
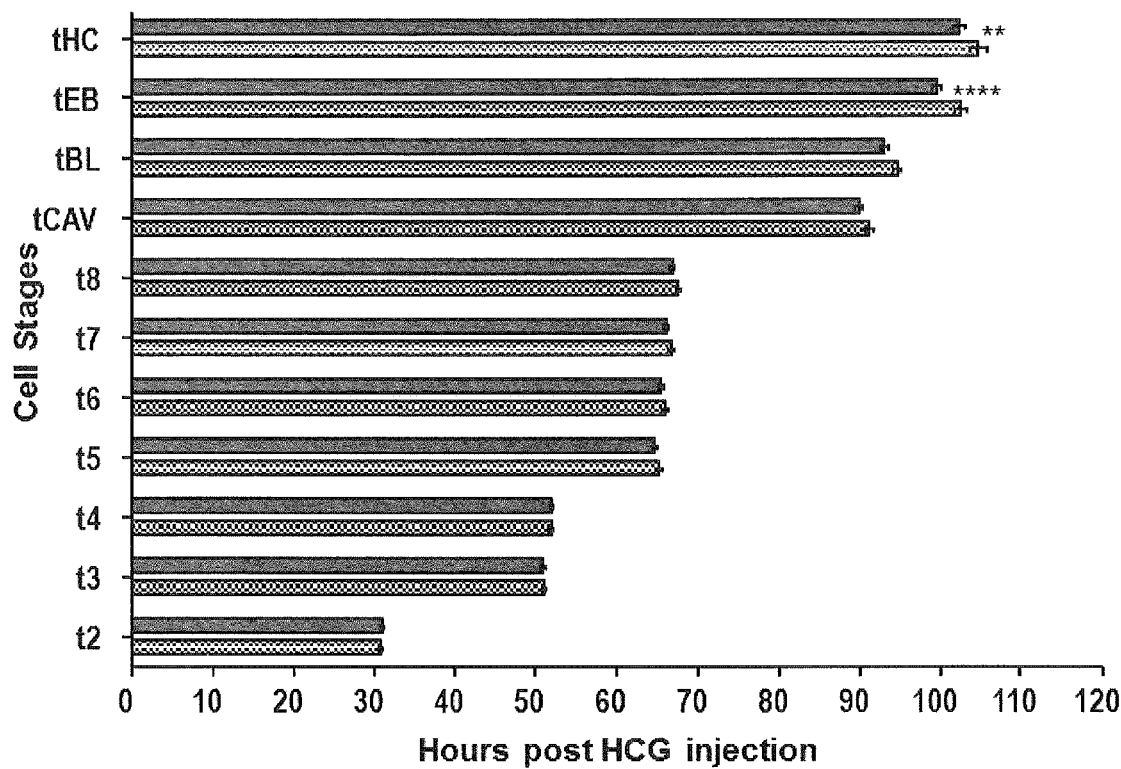
FIG. 5 shows timing of major developmental events expressed in hours post-hCG injection. tPNB=timing of pronuclei breakdown, t2=timing of 2-cell division, t3=timing of 3-cell, t4=timing of 4-cell division, t5=timing of 5-cells, t6=timing of 6 cell division, t8=timing of 8-cell division, tCA=time of cavitation (blastocoel starts formation), tB=time blastocyst forms, tE=time blastocyst is fully expanded, tH=time blastocyst hatches. Solid bars show controls, hatched grey bars show triple cocktail treated group , P<0.01; *, P<0.001; ****, P<0.0005. Data expressed as mean±SEM.
Figure 6:
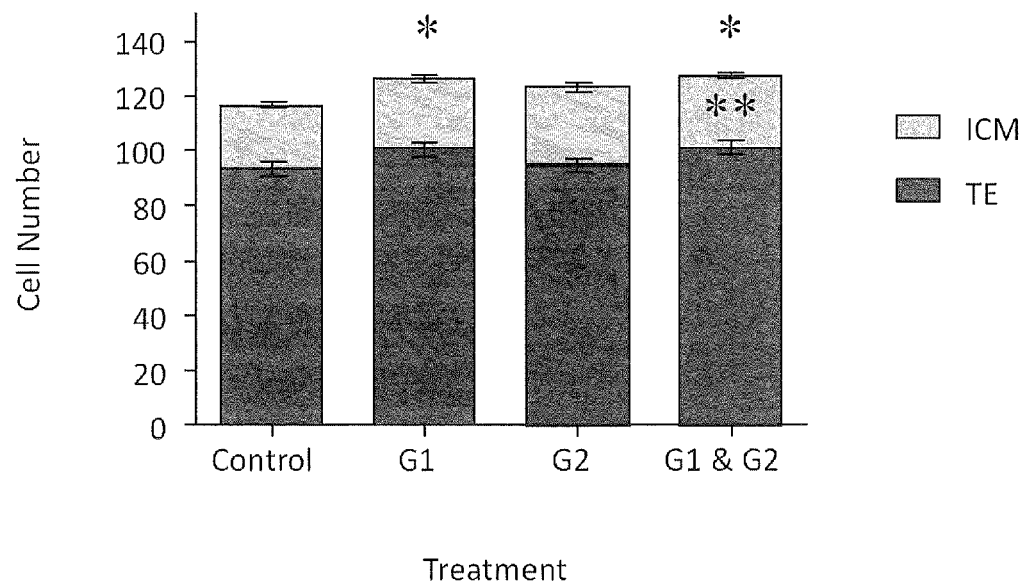
FIG. 6 shows the effect of the time of exposure to the triple cocktail on cell lineage allocation for embryos cultured groups in 20% oxygen. Cocktail comprises of 10 µM Carnitine, 10 µM Cysteine and 5 µM lipoic acid supplemented in media in the first 2 days (G1) or last 3 days (G2) or in both media (G1 & G2). Data are expressed as mean±SEM. Light and dark bar portions represent the average TE and ICM cells respectively. 3 biological replicates. Control (n=92), G1 (n=84), G2 (n=97), G1 & G2 (n=80). * P<0.05, ** P<0.01.

Example 5: Cleavage and Development Times of Individual Embryos Cultured with Triple Cocktail Embryo development kinetics were acquired using the PrimoVison (Vitrolife) using a dual-gas, thermostatted incubator fitted with bright field optics (MCOK-5M[RC], Sanyo, Osaka, Japan) and the EmbryoScope™ (Unisense FertiliTech) timelapse imaging systems. Embryos were cultured individually in control groups and in treatment groups at the optimal antioxidant dose and time lapse images were generated at 15 minute intervals throughout culture period. Morphokinetic event timings were recorded as hours post hCG administration. Cell cleavage and development times of embryos cultured individually in 20% O2 in media supplemented with antioxidant cocktail comprising of 10 μM Carnitine, 10 μM Cysteine and 5 μM lipoic acid 10 μM or in control media with no antioxidants (FIG. 5). Analysis of developmental kinetics revealed that embryos cultured in the triple cocktail group had significantly faster times to expanded (99.8±0.5 h vs. 102.8±0.7 h; P<0.05) and hatching blastocysts (102.6±0.8 h vs. 104.9±1.1 h; P<0.01) than embryos cultured in control groups (FIG. 5), indicating that the benefit of exposure to the antioxidants can been seen later in development as the blastocyst develops Example 6: Effect of Time Exposure to Compounds Effect of Time Exposure to Antioxidants
There was a significant increase in blastocyst inner cell mass number, leading to significant increase in total cell numbers of embryos grown in media supplemented with cocktail throughout the whole culture period up to 5 days (G1 & G2), compared to controls. There was also a significant increase in blastocyst total cell number of embryos grown in media supplemented in just medium G-1™ (FIG. 6) indicating a pre-compaction benefit.

Example 7: Correlation GSH Depletion Due to BSO Specificity

Optimal probe doses were found to be 200 μM buthionine sulfoximine (BSO) and 10 μM/ml monochlorobimane (MCB). BSO is an inhibitor of glutathione synthetase. MCB binds to reduced glutathione (GSH) and is a fluorescent marker of GSH used to measure GSH inside cells.

Figure 7:
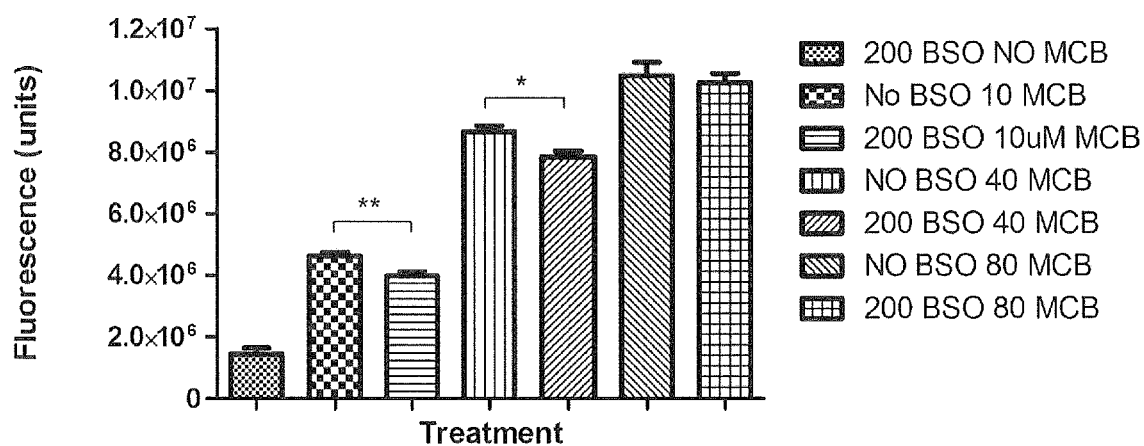
FIG. 7 shows the effect of BSO on MCB fluorescence—three biological replicates (n=6-12). **P=0.004, *P=0.011.

Embryos that were pre-treated with 200 μM BSO and subsequently treated with 10 μM/ml or 40 μmol/ml MCB showed significantly reduced fluorescence compared to groups treated with MCB only (FIG. 7). Results indicate high specificity binding of BSO to glutathione synthetase reducing the endogenous concentration of GSH thus resulting in lower fluorescence levels. The Figure shows a significant reduction in florescence in embryos treated with a combination of 200 μM BSO and either 10 μM or 40 μM MCB compared to embryos only treated with MCB. 10 μM MCB had greater reduced fluorescence (P=0.004) compared to 40 μM (P=0.011) hence this concentration (40 μM) was used in subsequent experiments. Interestingly at 80 μM MCB there were no significant differences in fluorescence between the BSO treated and non-BSO treated group indicating that at higher MCB concentrations fluorescence decrease owing to BSO sequestering could not be detected due to the high MCB fluorescence levels.

Example 8: Effect of Antioxidants on Embryonic GSH Levels

Figure 8:
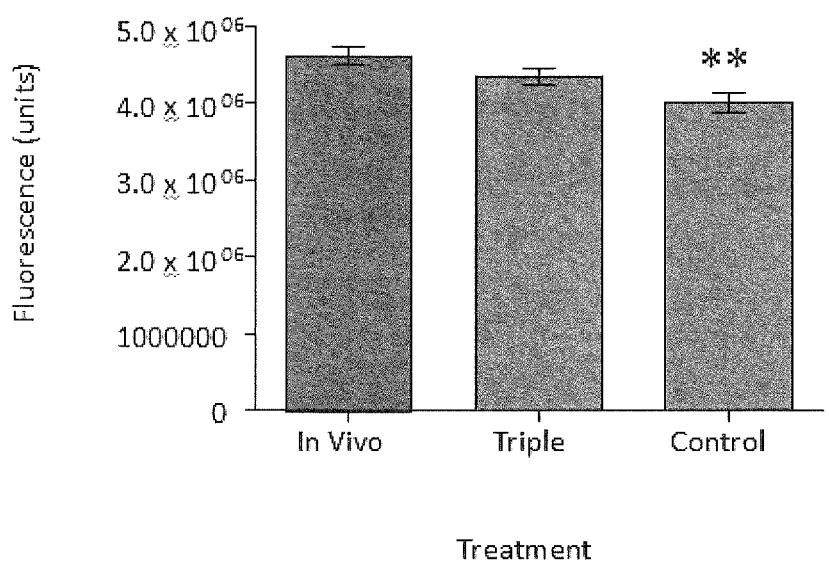
FIG. 8 shows fluorescence labelling of embryos with 10 uM MCB. Cocktail comprises of 10 µM Carnitine, 10 µM Cysteine and 5 µM lipoic acid. Data expressed as mean±SEM. Six biological replicates (n=60). Fluorescence values are shown in arbitrary units. **P<0.01.

Embryos were cultured in accordance with the material and methods section—see "Embryo culture for MCB and BSO treatment" and the glutathione (GSH) levels were determined during the "Determination of glutathione levels" in the material and methods section above. The Embryos in control groups that were cultured in the absence of the compounds (e.g. antioxidants) had significantly lower levels of GSH (P<0.01) compared to in vivo flushed embryos (FIG. 8). However when embryos were cultured with the triple antioxidant cocktail the levels of GSH was similar to that of in vivo developed embryos, indicating that antioxidants maintained the levels of GSH within the in vitro cultured embryos.

Example 9: Effect of Compounds on Fetal Development and Pregnancy (20% O$_2$)

Following transfer of blastocysts to pseudo pregnant recipients embryos that were cultured in the presence of antioxidants resulted in significantly longer crown-rump length (11.6±0.1 mm vs. 11.3±0.1 mm; P<0.01), heavier foetuses (209.8±11.8 mg vs. 183.9±5.9 mg; P<0.05) and placentas (103.5±3.1 mg vs. 93.6±2.7 mg; P<0.01) compared to controls (Table 2). There were no significant difference in implantation rate between control and triple antioxidant cultured embryos. Similarly morphological grading of limb, eye and ear and sex determination parameters showed no significant differences between the two groups.

TABLE 2

| Embryo transfer in 20% O$_2$ with triple cocktail | | |
|---|---|---|
| Parameter | Control | Triple |
| Implantation per transfer | 50.52 ± 8.52% | 61.05 ± 7.96% |
| Fetal development per transfer | 45.26% | 49.47% |
| Fetal weight (mg) | 183.9 ± 5.857 | 209.84 ± 11.808 [a] |
| Placental weight (mg) | 93.6 ± 2.737 | 103.5 ± 3.102 [b] |
| Crown-rump length (mm) | 11.27 ± 0.108 | 11.62 ± 0.090 [b] |
| Limb morphological grade | 14.76 ± 0.068 | 14.83 ± 0.064 |
| Eye morphological grade | 14.61 ± 0.105 | 14.55 ± 0.106 |
| Ear morphological grade | 14.51 ± 0.101 | 14.48 ± 0.103 |
| Sex of Fetus | 62.8% F, 32.6% M, 4.7% n/a, 2.3% Ex | 42.6% F, 53.2% M, 4.3% n/a, 2.1% Ex |

Data are expressed as % mean ± SEM.
n = 95 blastocyst transferred per group
F, female;
M, male;
n/a, undetermined;
Ex, Exencephalic
Letter within row represent significant differences between groups
[a] P < 0.05,
[b] P < 0.01,

Example 10: Effect of Compounds on Fetal Development and Pregnancy Of Embryos Cultured at 5% Oxygen and Compared to In Vivo Flushed Day 4 Embryos Following transfer of blastocysts to pseudo pregnant recipients, embryos that were in vivo flushed resulted in significantly heavier foetuses (P<0.0001) compared to embryos in control and triple antioxidant groups (Table 3). In addition in vivo flushed group foetuses had significantly longer crown to rump length (P<0.01) compared to the control group, however there were no differences compared to the triple group. Furthermore there were no significant differences in implantation rate, morphological grading of limb, eye and ear and sex parameters between the three groups.

TABLE 3

| Embryo transfer in 5% O$_2$ with triple cocktail | | | |
|---|---|---|---|
| Parameter | Control | Triple | In Vivo |
| Implantation per transfer | 56.67 ± 10.86% | 65.45 ± 6.38% | 64.44 ± 7.73% |
| Fetal development per transfer | 45.00% | 47.27% | 55.56% |
| Fetal weight (mg) | 198.08 ± 5.215 *** | 201.61 ± 5.172 *** | 240.08 ± 6.228 |
| Placental weight (mg) | 102.35 ± 6.808 | 96.35 ± 6.807 | 97.33 ± 4.167 |
| Crown-rump length (mm) | 11.22 ± 0.130 ** | 11.65 ± 0.118 | 11.86 ± 0.147 |
| Limb morphological grade | 14.93 ± 0.052 | 14.84 ± 0.096 | 15.04 ± 0.041 |
| Eye morphological grade | 14.89 ± 0.063 | 14.88 ± 0.068 | 14.96 ± 0.041 |

TABLE 3-continued

| Embryo transfer in 5% O₂ with triple cocktail | | | |
|---|---|---|---|
| Parameter | Control | Triple | In Vivo |
| Ear morphological grade | 14.87 ± 0.064 | 14.87 ± 0.070 | 15.00 ± 0.070 |
| Sex of Fetus | 55.6% F, 44.4% M | 30.77% F, 65.38% M, 3.85% Ex | 36% F, 64% M, |

Data are expressed as % mean ± SEM.
Blastocyst transferred per group: Control (n = 60), Triple (n = 55), In Vivo (n = 45)
F, female;
M, male;
Ex, Exencephalic
Significantly different from in vivo;
*** P < 0.0001,
Control is significantly different from in vivo;
** P < 0.01

Example 11: Effect of a Combination of Antioxidants for IVF Significantly Improves Embryo Development Oxidative stress occurs at all stages of human ART, with gametes being particularly susceptible to oxidative damage. We have shown that the combination of the antioxidants lipoate and carnitine (and optionally cysteine) in culture media was highly beneficial to embryo development.

In the present experimental work we show that the presence of antioxidants during IVF was also beneficial. We therefore examined the effects of this group of antioxidants during oocyte and sperm collection and IVF.

Materials and Methods:

Gamete collection from F1 mice and IVF were conducted in 20% oxygen in the presence or absence of 10 µM acetyl-L-carnitine/10 µM N-acetyl-L-cysteine/5 µM α-lipoic acid. The resulting embryos were individually cultured in media G-1™ & G-2™ with or without antioxidants, creating four groups. Embryo development was analysed by time-lapse microscopy followed by differential nuclear staining to determine cell allocation to the blastocyst.

Total cell and inner cell mass (ICM) numbers in the control were 32.9±2.1 and 7.7±2.1 respectively. Addition of antioxidants exclusively in the medium for IVF resulted in a significant increase in total numbers (48.7±2.8; P<0.01). Antioxidants present solely in the embryo culture media resulted in a significant increase in total cell numbers (50.4±3.2; P<0.001). However, the presence of antioxidants in both the IVF medium and embryo culture media resulted in significant increases in both total blastocyst and ICM cell numbers (59.8±3.4, 15.3±1.1; P<0.01). Subsequent time-lapse analysis on the IVF derived embryos revealed that antioxidant treatment during IVF and culture was associated with faster developmental times to 5 cell cleavage (51.8±0.6 h vs. 54.1±0.7 h) which continued through to expanded blastocyst stage. In conclusion, the presence of antioxidants during IVF and throughout embryo culture imparts significant beneficial effects on embryo development rate and subsequent cell numbers and allocation. These findings indicate that supplementation of antioxidants to the IVF medium, as well as to embryo culture, will further assist in maintaining the viability of human embryos in ART, plausibly through the reduction of oxidative stress.

In a separate study, pronucleate embryos were collected in the presence or absence of antioxidants in the gamete handling media, namely G-MOPS™, and cultured in control media with no antioxidants. The fertilisation media used for IVF was G-IVF™, the embryo culture medium used to culture the embryos from one cell to blastocyst was in G-1™ & then G-2™ media (G-1™ was for day 1 for 48 h & G-2™ was for day 3 for 48 h). Embryo development was analysed by differential cell staining.

Figure 9:
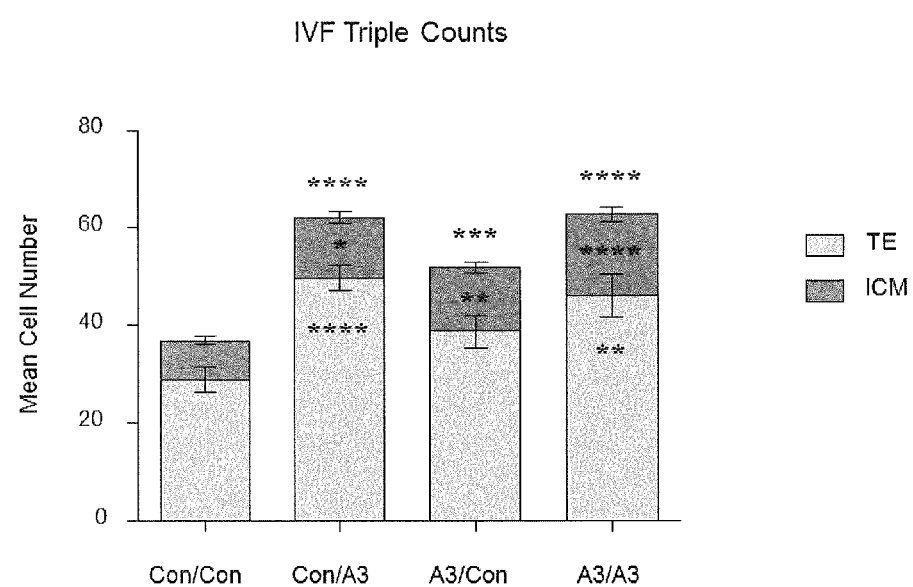
FIG. 9 shows the effect of combined antioxidants on blastocyst cell numbers of IVF embryos cultured in individually at 20% oxygen. Data are expressed as mean±SEM. Light and dark bar portions represent the average TE and ICM cells respectively. Cell lineage allocation of embryos cultured individually in 20% oxygen. Antioxidants (A3) were in gamete handling/collection media and/or culture media. Controls (Con) were in gamete and/or culture media with no antioxidants: 4 biological replicates. Con/Con (n=34), Con/A3 (n=34), A3/Con (n=38), A3/A3 (n=48). *P<0.05, P<0.01, *P<0.001, ****P<0.0001.
Figure 10:
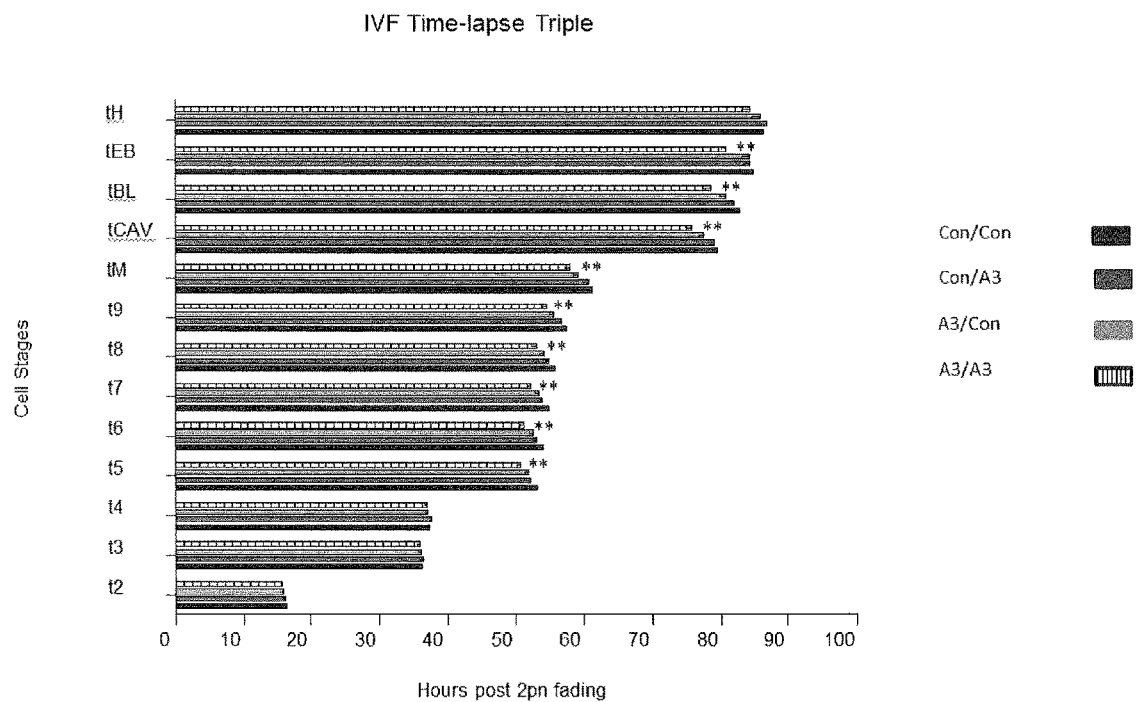
FIG. 10 shows the effect of combined antioxidants on IVF derived blastocyst cultured in individually at 20% oxygen—Data are expressed as mean±SEM. Antioxidants (A3) were in gamete handling/collection media and/or culture media. Controls (Con) were in gamete handling media and/or culture media with no antioxidants. 3 biological replicates, Con/Con (n=34), Con/A3 (n=34), A3/Con (n=38), A3/A3 (n=48). **P<0.01.

Results:

Addition of antioxidants exclusively in gamete handling media for IVF resulted in embryos with significantly increased blastocyst cell numbers compared to controls (48.9±3.3 vs. 33.6±2.1; P<0.001) (see FIG. 9). Similarly antioxidants present solely in the embryo culture media resulted in significantly increased blastocyst cell numbers compared to controls (59.3±3.1 vs. 33.6±2.1; P<0.001)) (see FIG. 9). The presence of antioxidants during both gamete collection and embryo culture also resulted in further significant increases in blastocyst cell numbers compared to controls (61.0±3.9 vs. 33.6±2.1; P<0.001) (see FIG. 9). Subsequent time-lapse analysis on the IVF derived embryos revealed that antioxidant treatment during both collection and culture was associated with faster developmental times to 5 cell cleavage (51.8±0.6 h vs. 54.1±0.7 h) which continued through to blastocyst stage (see FIG. 10). In an independent study, pronucleate oocytes treated with antioxidants for 20 minutes during embryo collection resulted in significantly increased blastocyst inner cell mass numbers compared to controls (19.3±1.2 vs. 16.2±1.1; P<0.05).

Conclusion:

Inclusion of antioxidants during gamete preparation and IVF and also throughout the culture period has beneficial outcomes on embryo cell numbers and development rate. These findings indicate that supplementation of antioxidants to oocyte and sperm preparation/handling media and IVF media, as well as to embryo culture, will further assist in the development and viability of human embryos in ART by reducing oxidative stress.

Example 12: Effect of a Combination of Antioxidants Significantly Improves Human Embryo Development In Vitro In the present experimental work we show that the presence of antioxidants was beneficial to human embryo development in vitro. We examined the effects of a group of antioxidants, namely 10 µM Acetyl Carnitine, 10 µM Acetyl Cysteine and 5 µM Lipoic acid during embryo development in vitro.

Materials and Methods

For the experimental group the antioxidants (10 µM acetyl-L-carnitine/10 µM N-acetyl-L-cysteine/5 µM α-lipoic acid) were added to the Vitrolife medium G-IVF which was used for human oocyte retrieval and fertilisation and to protein supplemented G1 and G2 media (available from Vitrolife) which were used for human embryo culture, media was changed from G-1 to G-2 on day three.

The embryos were cultured in 5% oxygen.

Embryo development was assessed by time-lapse microscopy and embryo quality was measured on day 5 by a defined blastocyst scoring system (see Gardner et al 1999 In vitro culture of human blastocyst In Jansen R and Mortimer D (eds) *Towards reproductive certainty: fertility* and *genetics beyond* 1999. Parthenon Publishing Carnforth, UK, pp. 378-388)). The final outcome parameters were utilisation rate and embryo quality at the blastocyst stage.

Figure 13:
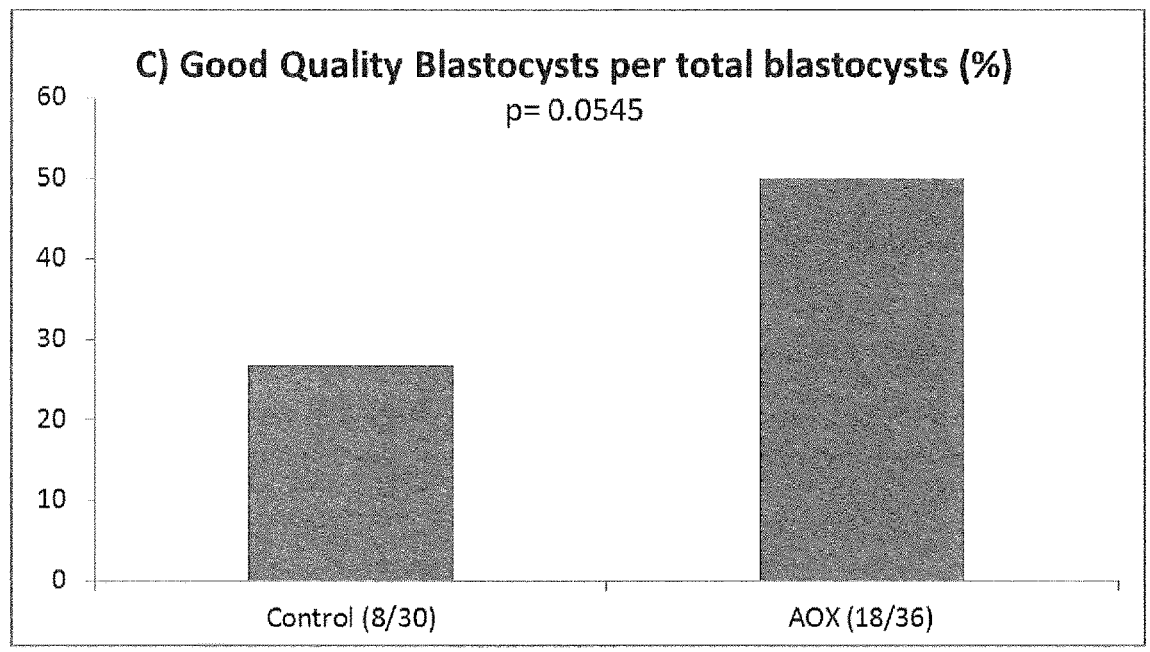
FIG. 13 shows the proportion of human blastocysts in percent reaching the score of Good Quality Blastocyst (GQB), equalling to a score of 3AB or higher according to the Gardner blastocyst grading system, per total number of blastocysts. In the control group 8 out of 30 blastocysts were graded GQB in the group cultured in media supplemented with 10 µM Acetyl Carnitine, 10 µM Acetyl Cysteine and 5 µM Lipoic acid 18 out of 36 were graded GQB. The large difference between the two groups is illustrated by the p-value of 0.0545 applying a two-tailed t-test using commercially available software (GraphPad Prism).

Results:

Addition of antioxidants in embryo culture media resulted in more Good Quality Blastocysts (i.e. the fraction of blastocysts that reached a quality score of 3AB or higher according to the Gardner Scoring System (see Gardner et al 1999). compared with embryos cultured in comparable media without antioxidants (see FIG. 13). FIG. 13 shows the proportion of blastocysts in percent reaching the score of Good Quality Blastocyst (GQB), according to the Gardner blastocyst grading system, per total number of blastocysts. In the control group 8 out of 30 blastocysts were graded GQB in the group cultured in media supplemented with 10 µM Acetyl Carnitine, 10 µM Acetyl Cysteine and 5 µM Lipoic acid 18 out of 36 were graded GQB. The large difference between the two groups is illustrated by the p-value of 0.0545 applying a two-tailed t-test using commercially available software (GraphPad Prism).

Figure 11:
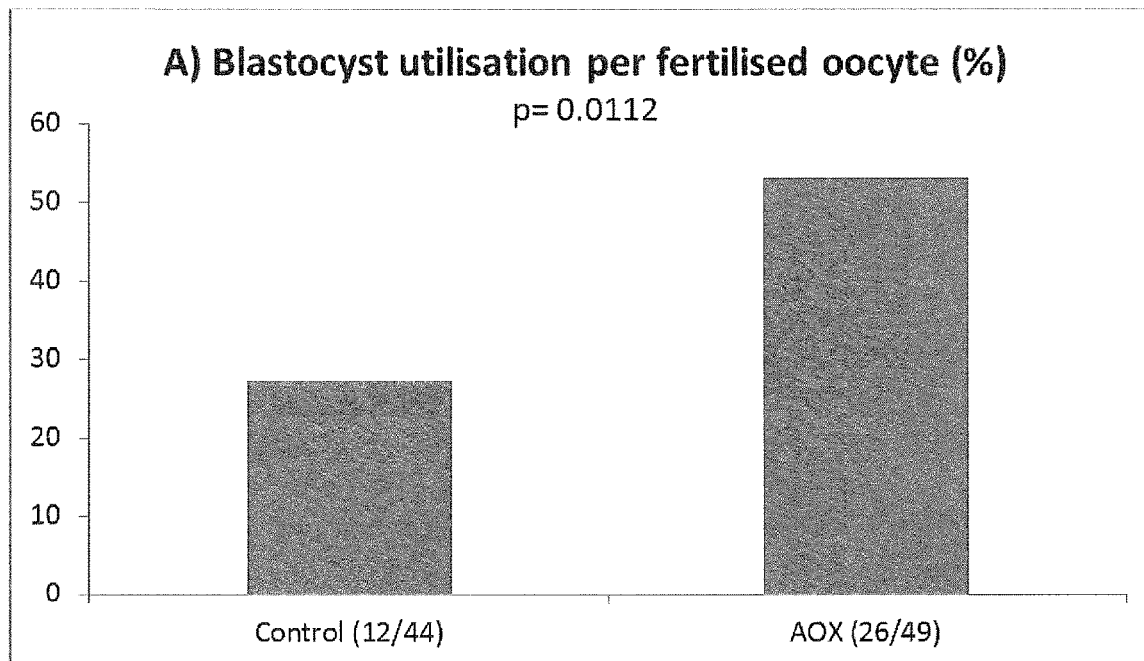
FIG. 11 shows human blastocyst utilisation rate in percent of total number of fertilised oocytes. In the control group 12 out of 44 fertilised oocytes were selected for further clinical use, in the group cultured in media supplemented with 10 µM Acetyl Carnitine, 10 µM Acetyl Cysteine and 5 µM Lipoic acid 26 out of 49 were selected for further clinical therapeutic use. Blastocysts not fulfilling the quality requirements were not selected and discarded. The difference between the two groups was significant with a p-value of 0.0112 applying a two-tailed t-test using commercially available software (Graph Pad Prism).

In addition antioxidants significantly increased blastocyst utilization rate (i.e. the fraction of blastocysts that are either used fresh for transfer or cryopreserved for later transfer to the patient—(see FIG. 11 and FIG. 12). FIG. 11 shows blastocyst utilisation rate in percent of total number of fertilised oocytes. In the control group 12 out of 44 fertilised oocytes were selected for further clinical use, in the group cultured in media supplemented with 10 µM Acetyl Carnitine, 10 µM Acetyl Cysteine and 5 µM Lipoic acid 26 out of 49 were selected for further clinical therapeutic use. Blastocysts not fulfilling the quality requirements were not selected and discarded. The difference between the two groups was significant with a p-value of 0.0112 applying a two-tailed t-test using commercially available software (GraphPad Prism).

Figure 12:
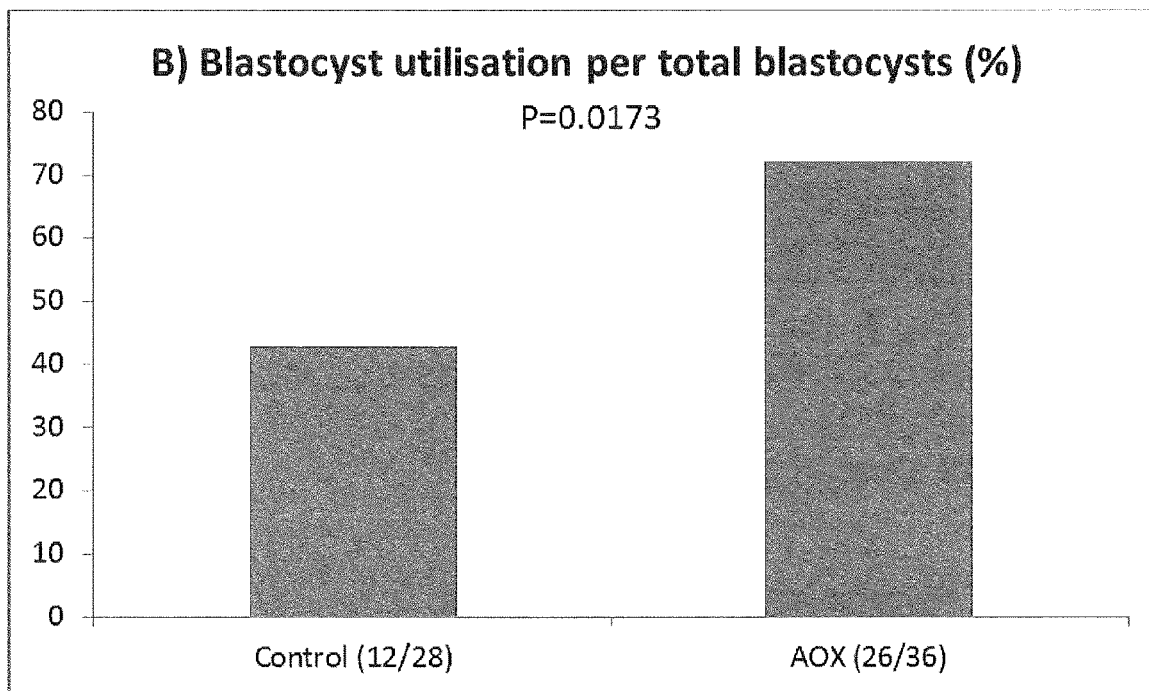
FIG. 12 shows human blastocyst utilisation rate in percent of total number of blastocysts. In the control group 12 out of 28 blastocysts were selected for further clinical use, in the group cultured in media supplemented with 10 µM Acetyl Carnitine, 10 µM Acetyl Cysteine and 5 µM Lipoic acid 26 out of 36 were selected for further clinical therapeutic use. Blastocysts not fulfilling the quality requirements were not selected and discarded. The difference between the two groups was significant with a p-value of 0.0173 applying a two-tailed t-test using commercially available software (Graph Pad Prism).

FIG. 12 shows blastocyst utilisation rate in percent of total number of blastocysts. In the control group 12 out of 28 blastocysts were selected for further clinical use, in the group cultured in media supplemented with 10 µM Acetyl Carnitine, 10 µM Acetyl Cysteine and 5 µM Lipoic acid 26 out of 36 were selected for further clinical therapeutic use. Blastocysts not fulfilling the quality requirements were not selected and discarded. The difference between the two groups was significant with a p-value of 0.0173 applying a two-tailed t-test using commercially available software (GraphPad Prism).

Conclusion:

Inclusion of antioxidants during oocyte retrieval, fertilisation and embryo culture in vitro has beneficial outcomes on the quality of the blastocysts. In particularly the use of antioxidants resulted in more blastocysts of better quality which can be used for therapy.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An embryo culture medium, or gamete culture medium comprising:
    a) acetyl-carnitine at a concentration of 5 µM to 20 µM; and
    b) lipoic acid or a derivative thereof at a concentration of 5 µM to 10 µM; and
    c) acetyl-cysteine at a concentration of 5 µM to 20 µM.

2. The medium according to claim 1, wherein the medium further comprises one or more of: an inorganic salt, energy source, amino acid, protein, cytokine, chelating agent, antibiotic, hyaluronan, growth factor, hormone, vitamin and granulocyte-macrophage colony-stimulating factor (GM-CSF).

3. The culture medium according to claim 1, that improves the success rate of in vitro fertilisation.

4. The medium according to claim 1, wherein the concentration of acetyl-carnitine is 10 µM.

5. The medium according to claim 1, wherein the concentration of acetyl-cysteine is 10 µM.

6. The medium according to claim 1, wherein the concentration of lipoic acid or a derivative thereof is 5 µM.

7. A method of reducing or preventing oxidative stress and/or free radical formation, and/or increasing levels of antioxidant capacity in an embryo, or a gamete cultured in vitro and/or improving the development of an embryo cultured in vitro or improving the health and viability of a gamete or improving the fertilization of an oocyte by a sperm, and/or for in vitro fertilization, the method comprising handling and/or manipulating and/or culturing the embryo and/or gamete, in a medium according to claim 1.

8. The method according to claim 7, wherein the improvement in development of an embryo comprises:
    a) an increase in trophectoderm cell number, inner cell mass and/or total cell number in the embryo at the blastocyst stage;
    b) a reduced time to reach expanded blastocyst and hatching development;
    c) an increase in fetal weight, fetal crown-rump length and/or placental weight after embryo transfer;
    d) an increase in good quality blastocysts, wherein the blastocysts have reached a quality score of 3AB or higher according to the Gardner Scoring System; and/or
    e) an increase in blastocyst utilization rate.

9. The method according to claim 7, wherein the embryo is a mammalian embryo.

10. The method according to claim 7, wherein the embryo is cultured individually.

11. The method according to claim 10, wherein the embryo is cultured to the blastocyst stage.

12. The method according to claim 7, wherein the embryo or gamete is handled and/or manipulated and/or cultured under in an environment with an oxygen content of between 5-20%.

* * * * *

UNITED STATES PATENT AND TRADEMARK OFFICE
CERTIFICATE OF CORRECTION

| | |
|---|---|
| PATENT NO. | : 11,639,494 B2 |
| APPLICATION NO. | : 15/754679 |
| DATED | : May 2, 2023 |
| INVENTOR(S) | : Thi Truong et al. |

Page 1 of 1

It is certified that error appears in the above-identified patent and that said Letters Patent is hereby corrected as shown below:

In the Claims

At Column 28, Line 59, "claim 10," should be -- claim 7, --.

Signed and Sealed this
Seventh Day of November, 2023

Katherine Kelly Vidal
*Director of the United States Patent and Trademark Office*